(12) United States Patent
Phanstiel, IV et al.

(10) Patent No.: US 7,910,363 B1
(45) Date of Patent: Mar. 22, 2011

(54) LIPOPHILIC POLYAMINES PROVIDING ENHANCED INTRACELLULAR DELIVERY OF AGENTS BY A POLYAMINE TRANSPORT SYSTEM

(75) Inventors: Otto Phanstiel, IV, Oviedo, FL (US);
Ken Teter, Oviedo, FL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 0 days.

(21) Appl. No.: 12/113,970

(22) Filed: May 2, 2008

Related U.S. Application Data

(60) Provisional application No. 60/915,492, filed on May 2, 2007.

(51) Int. Cl.
*C12N 15/00* (2006.01)
*A01N 63/00* (2006.01)

(52) U.S. Cl. ............... 435/320.1; 435/455; 424/93.21; 514/44

(58) Field of Classification Search ............... None
See application file for complete search history.

(56) References Cited

OTHER PUBLICATIONS

Gardener et al. J Med Chem 50:308-318; Jan. 2005.*

* cited by examiner

*Primary Examiner* — James (Doug) Schultz
(74) *Attorney, Agent, or Firm* — Allen, Dyer, Doppelt, Milbrath & Gilchrist, P.A.

(57) ABSTRACT

Polyamine cationic lipids have been synthesized that have the ability to be transported into cells having an active polyamine transport system. Accordingly, these lipids may be conjugated with various agents and, thereby, act as vectors for transporting the agent into the cell aided by the cell's own polyamine transport system. A method of delivering an agent into a cell includes associating the agent with a polyamine cationic lipid selected from compounds 25, 26, 27, 28, their pharmaceutically acceptable salts and combinations thereof and contacting the cell therewith.

32 Claims, 8 Drawing Sheets

Scheme 1[a]

[a]Reagents: a) K₂CO₃, KI, cyclohexanone; b) KOH, EtOH; c) oxalyl chloride

Scheme 2[a]

[a]Reagents: a) BOC₂O (0.33 equiv), MeOH, NEt₃; b) Br(CH₂)₃CN, K₂CO₃, CH₃CN; c) BOC₂O (1.5 equiv), MeOH, NEt₃; d) H₂, Raney Ni, EtOH, NH₄OH; e) BOC₂O, THF Scheme 3ᵃ. Synthesis of the lipid-polyamine conjugates 15-19

ᵃReagents: a) respective amine, CH₂Cl₂, MeOH; b) NaBH₄

Scheme 4ᵈ.

ᵃReagents: a) 12 or 14, CH₂Cl₂, 1M NaOH

Scheme 5[a].

[a]Reagents: a) anhydrous HCl in ethyl acetate

LIPOPHILIC POLYAMINES PROVIDING ENHANCED INTRACELLULAR DELIVERY OF AGENTS BY A POLYAMINE TRANSPORT SYSTEM

RELATED APPLICATION

This application claims priority from provisional application Ser. No. 60/915,492, which was filed on May 2, 2007 and which is incorporated herein by reference in its entirety.

FIELD OF THE INVENTION

This invention relates to polyamines and, more specifically, to lipophilic polyamines effective in entering cells having an active polyamine transport system.

BACKGROUND OF THE INVENTION

With the information gained by the sequencing of the human genome,[1,2] gene therapy now holds promise for the treatment of hereditary diseases and cancers.[3,4] It is now possible to silence a bad gene[5], turn on a needed gene[6], or install a new gene to address particular cellular defects.[7] However, a key requirement for successful gene therapy is the efficient transfer of DNA to specific cell types in vivo. Viral vectors have proven to be very efficient transfection agents and allow for the insertion of foreign DNA into many cell types.[8,9] However, the inherent problems with viral vectors such as immunogenicity and the limited size of the DNA plasmid that can be transferred has led to interest in developing efficient non-viral vectors.[10-14] Non-viral vectors are ideal because of their expected low toxicity and immunogenicity, ability to transfer large strands of DNA and simpler synthetic preparation. Typically, these vectors consist of a lipophilic component attached to a positively charged, polar headgroup, through the use of a spacer or linking motif, and are a mixture of neutral and positively charged lipids. A wide range of cationic liposomes have been synthesized and recently reviewed.[15-17] The cationic headgroups typically found in these liposome systems include quaternary ammonium salts,[10] polylysine,[18] polyguanadinium salts,[19] polyarginine[20] and polyamines.[21]

Polyamines were introduced into liposomes by Behr,[22] when it was realized that the naturally-occurring polyamines such as spermidine and spermine (FIG. 1) could efficiently compact DNA. Behr went on to synthesize one of the first transfection vectors, DOGS 1, and incorporated a branched polyamine as the polar headgroup (FIG. 2).[11]

Following this work, a number of research groups have looked at the effect of changing the positively-charged, polyamine headgroup on cationic liposomes with respect to their efficiency at transfecting DNA.[15,16,21,23,24] Byk et al[21] showed that when assayed in HeLa cells, the compound RPR 120535 2, whose configuration of the polar head is linear, was 5-10 times more effective at transfection than those with branched-, globular- or T-shaped polar domains. Safinya et al[24] demonstrated with 3 that lipids containing a higher number of positive charges had better transfection efficiency within a series of liposomes containing branched-polyamine headgroups. Other popular vectors 4-6 are shown in FIG. 2. Commercially-available Lipofectamine is a 3:1 mixture of 4 and 6.[18b]

Although a large number of cationic lipids have been surveyed, a systematic study of how linear polyamine architectures effect transfection efficiency is still needed, especially in light of the molecular recognition elements required to use the polyamine transporter (PAT) for cellular entry.[25-32] Our goal was to perform the key crossover experiments needed to tie these two fields together. Indeed, understanding how cationic motifs are transported across the cell membrane is critical to both enterprises.

Targeting a specific cellular transporter could provide cell-selective transfection. For example, rapidly-proliferating cancer cells could be targeted via their PAT, which is often up-regulated.[28] Indeed, the ability to transfect a specific cell type would have profound impact on a multitude of gene therapy strategies.

Since many cancer cell lines have active polyamine transporters, it is possible to target these cells using the molecular recognition events involved in polyamine import.[28] For example, an anthracene-homospermidine conjugate was shown to be 10-30 fold more toxic to B16 melanoma cells than to 'normal' melanocytes (Mel-A cells).[28] A multitude of polyamine structures were previously screened for their high PAT selectivity in CHO and CHO-MG cells.[28] Several linear polyamine architectures were identified, which selectively targeted the PAT-active CHO cell line over its PAT-inactive CHO-MG mutant.[25-32] The discovery of homospermidine, a 4,4-triamine, as a cell-selective 'vector' motif provided the means to test the PAT-delivery system as a conduit for gene delivery.[26,28]

In short, our aim was to combine these two areas of research (PAT targeting and gene delivery) by attaching PAT-targeting polyamine sequences[28] to aryl lipid motif 3[24] in order to facilitate DNA plasmid uptake. These materials were then evaluated for their DNA-transporting ability as well as transfection efficacy and compared to the commercially-available transfection reagent, Lipofectamine 2000.[33]

SUMMARY OF THE INVENTION

With the foregoing in mind, the present invention advantageously provides a vector effective in delivering an agent into a cell, said vector comprises a cationic lipid selected from compounds according to formulas 25, 26, 27, 28, their pharmaceutically acceptable salts and combinations thereof.

Another embodiment of the invention includes a polyamine cationic lipid vector effective in delivering an agent into a cell in enhanced levels by being recognized by the cell's polyamine transport system, said vector comprises compound 26 or a pharmaceutically acceptable salt thereof.

A preferred method of the invention includes delivering an agent into a cell, the method comprises associating the agent with a polyamine cationic lipid selected from compounds 25, 26, 27, 28, their pharmaceutically acceptable salts and combinations thereof and contacting the cell therewith.

A further method of the invention includes delivering enhanced levels of an agent into a cell, the method comprises associating the agent with a polyamine cationic lipid according to compound 26 or a pharmaceutically acceptable salt thereof and effective in being recognized by a polyamine transport system in the cell.

The invention also includes a method of delivering enhanced levels of an agent into target cells having an upregulated polyamine transporter, the target cells being among a population of normal cells, the method comprises associating the agent with a polyamine cationic lipid according to compound 26 or a pharmaceutically acceptable salt thereof and contacting the cell population therewith so as to preferentially deliver the polynucleotide into the target cells via the upregulated polyamine transporter system.

Yet another method of the invention is for treating a target cell having an upregulated polyamine transporter, the method comprises associating an agent with a polyamine cationic lipid according to compound 26 or a pharmaceutically acceptable salt thereof and contacting the cell therewith.

BRIEF DESCRIPTION OF THE DRAWINGS

Some of the features, advantages, and benefits of the present invention having been stated, others will become apparent as the description proceeds when taken in conjunction with the accompanying drawings, presented for solely for exemplary purposes and not with intent to limit the invention thereto, and in which.

DETAILED DESCRIPTION OF PREFERRED EMBODIMENTS

Figure 1:
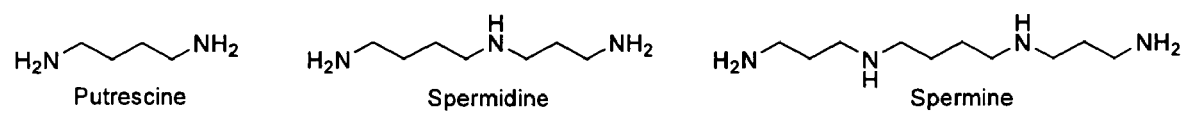
FIG. 1 shows naturally occurring polyamines, as known in the prior art.

The present invention will now be described more fully hereinafter with reference to the accompanying drawings, in which preferred embodiments of the invention are shown. Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. Any publications, patent applications, patents, or other references mentioned herein are incorporated by reference in their entirety. In case of conflict, the present specification, including any definitions, will control. In addition, the materials, methods and examples given are illustrative in nature only and not intended to be limiting. Accordingly, this invention may, however, be embodied in many different forms and should not be construed as limited to the illustrated embodiments set forth herein. Rather, these illustrated embodiments are provided so that this disclosure will be thorough and complete, and will fully convey the scope of the invention to those skilled in the art. Other features and advantages of the invention will be apparent from the following detailed description, and from the claims.

As used herein, the term "pharmaceutically acceptable salt or prodrug" is intended to describe any pharmaceutically acceptable form (such as a salt of these amine systems with an organic carboxylic acid like acetic acid or toluene-sulfonic acid or methane sulfonic acid or an inorganic acid such as HCl, HBr, phosphoric acid, or a related group or prodrug) of a compound of the invention, which, upon administration to a subject, provides the mature or base compound (e.g., the lipophilic polyamine compound). Pharmaceutically acceptable salts include those derived from pharmaceutically acceptable inorganic or organic bases and acids. Suitable salts include those derived from alkali metals such as potassium and sodium, alkaline earth metals such as calcium and magnesium, among numerous other acids well known in the pharmaceutical art. Pharmaceutically acceptable prodrugs refer to a compound that is metabolized, for example hydrolyzed or oxidized, in the host to form the compound of the present invention. Typical examples of prodrugs include compounds that have biologically labile protecting groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, dephosphorylated to produce the active compound.

Results and Discussion
Synthesis.

A series of derivatives were synthesized with a variety of linear polyamine headgroups. These cationic headgroups contained from two to four positive charges. The convergent synthetic route involved: a) the synthesis of the hydrophobic lipid moiety, b) the synthesis of the BOC-protected amine head groups, c) coupling of the two separate components followed by d) the deprotection of the polyamine moiety to furnish the final compounds as HCl salts.

Figure 2:
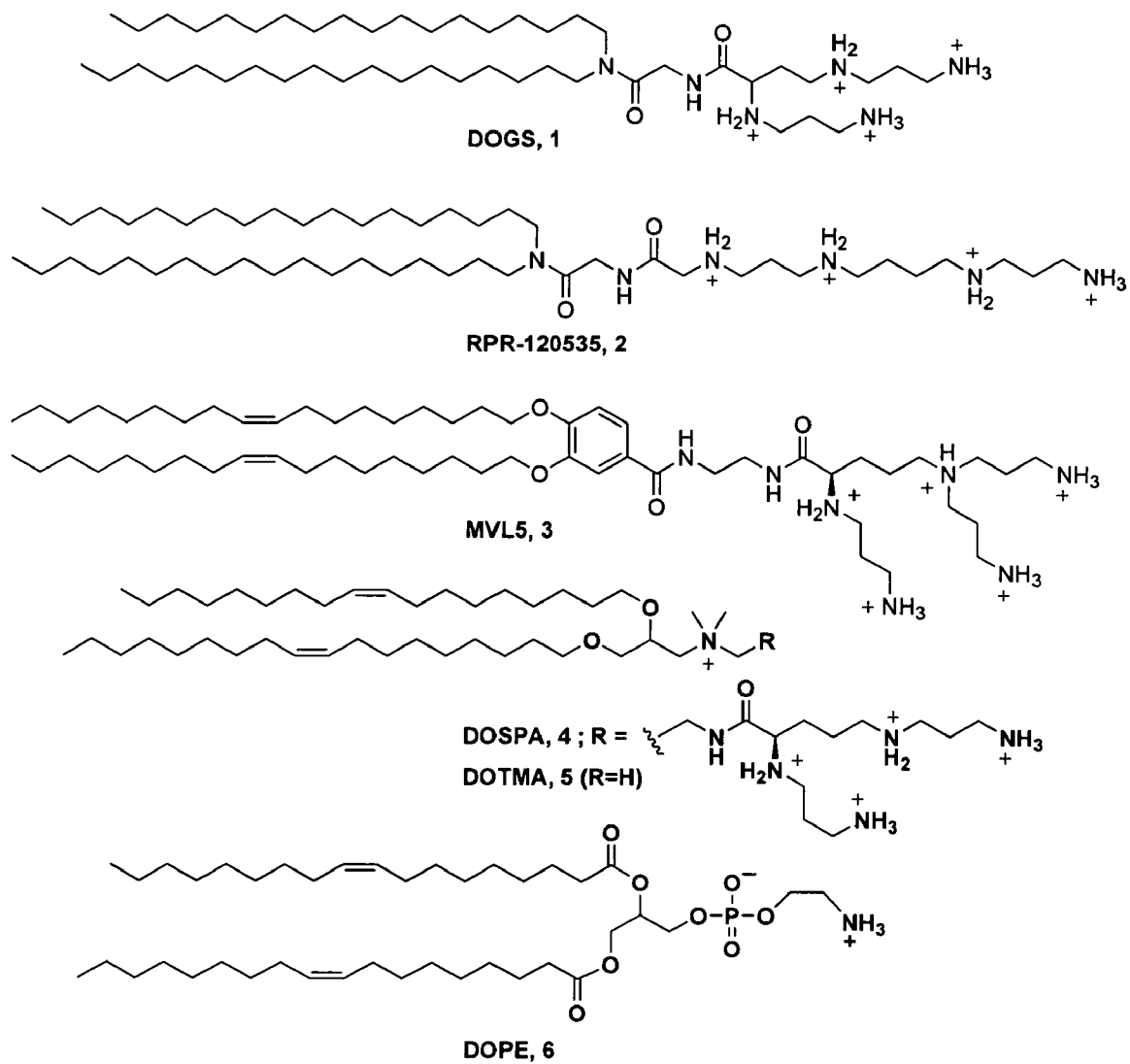
FIG. 2 illustrates additional previously known polyamines.

The 3,4-disubstituted benzene containing lipids were chosen due to the significant success of these lipids in earlier transfection studies by Safinya and others.[10,23,24] This structural element is also present in DOSPA 4 and DOTMA 5 (FIG. 2). The unsaturated unit within the C18 chain was shown to prevent side chain recrystallisation and conferred a high degree of flexibility upon the cationic liposomes. These side chains were attached to the central benzene core via ether linkages. An aldehyde or acid chloride in position 1 allowed for attachment of the polyamine component. The polyamine scaffolds and controls were identified in earlier investigations of PAT-mediated drug delivery.[25-29]

Figure 3:
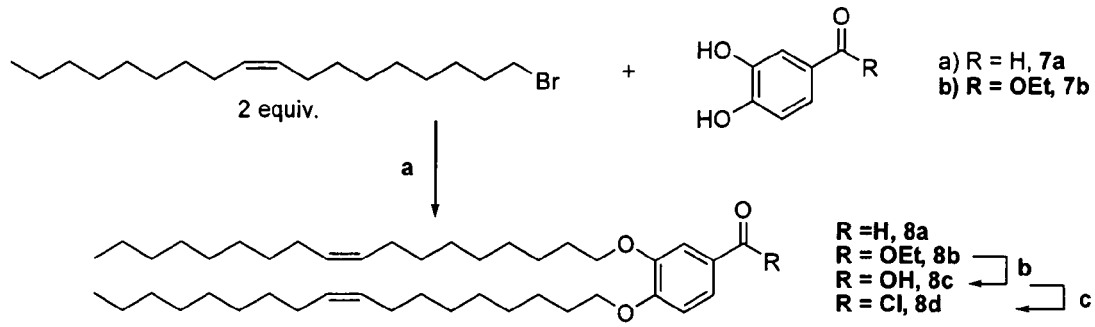
FIG. 3 is a diagram of synthetic scheme 1 of the present invention.

The first step was the synthesis of 3,4-di(oleyloxy)benzaldehyde 8a by the O-alkylation of 3,4-dihydroxy benzaldehyde 7a with oleyl bromide (Scheme 1 as shown in FIG. 3). Similarly, the bis-O-alkylation of ethyl 3,4-dihydroxybenzoate 7b with oleyl bromide was used to form ethyl 3,4-di(oleyloxy)benzoate 8b using the method of Safinya et al.,[23,24] Subsequent cleavage of 8b with KOH was carried out to give the acid 8c (Scheme 1) followed by treatment with oxalyl chloride to give the desired acid chloride 8d.

Figure 4:
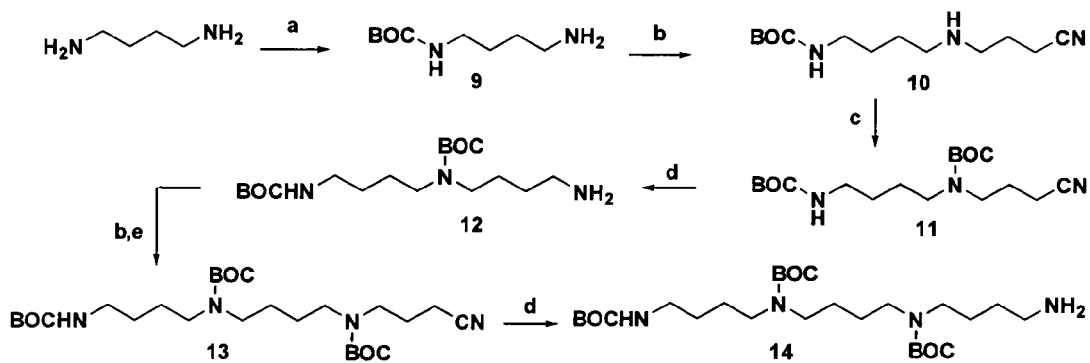
FIG. 4 diagrams synthetic scheme 2 of the present invention.

As shown in Scheme 2 (FIG. 4), the next step in the synthesis involved the generation of the polyamine moieties: $N^1$-(tert-butoxycarbonyl) putrescine 9, $N^1,N^4$-di-(tert-butoxycarbonyl) homospermidine $12^{34}$ and $N^1,N^4,N^8$-tri-(tert-butoxycarbonyl) homospermine 14 (Scheme 2). The mono BOC protection of diaminobutane gave the amine 9 in a good yield. Sequential addition of bromobutyronitrile, BOC protection of the newly formed secondary amine, followed by reduction of the nitrile with Raney Ni gave masked triamine 12. Repetition of these three steps on 12 gave tri-BOC-protected tetraamine 14.

Figure 5:
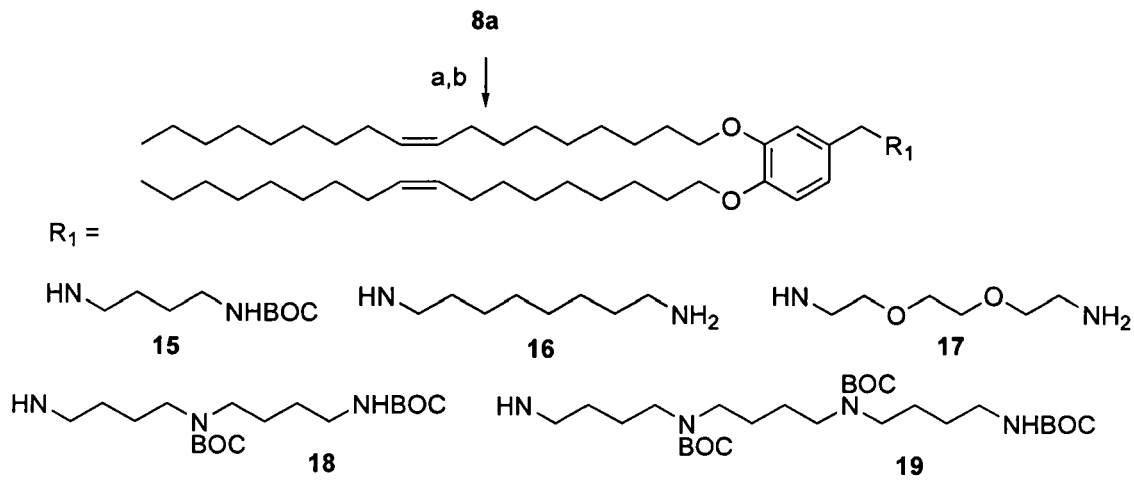
FIG. 5 shows the flow of synthetic scheme 3 of the present invention.
Figure 6:
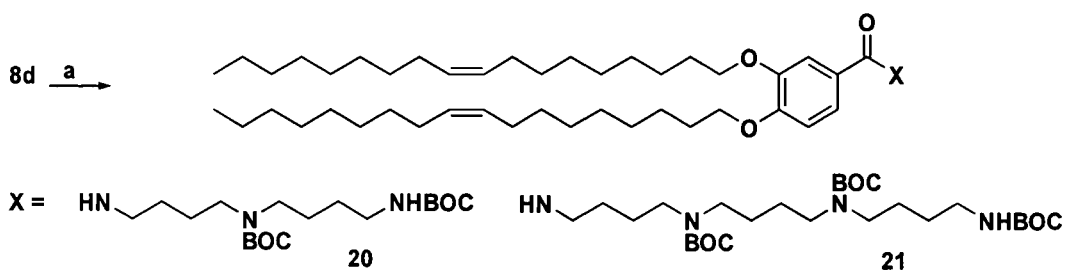
FIG. 6 shows synthetic scheme 4 of the present invention.

The coupling of the aldehyde 8a to a range of polyamines was based on previous procedures for coupling of amines to benzaldehyde derivatives.[25-28] As shown in Scheme 3 (shown in FIG. 5), the reductive amination of 8a was achieved in two steps via in situ generation of the imine (with a series of amines) followed by reduction using $NaBH_4$ to give the respective 2° amines (15-19). As shown in Scheme 4 (shown in FIG. 6), the respective polyamines 12 and 14 were coupled to acid chloride 8d to provide the BOC-protected benzamide systems, 20 and 21.

Figure 7:
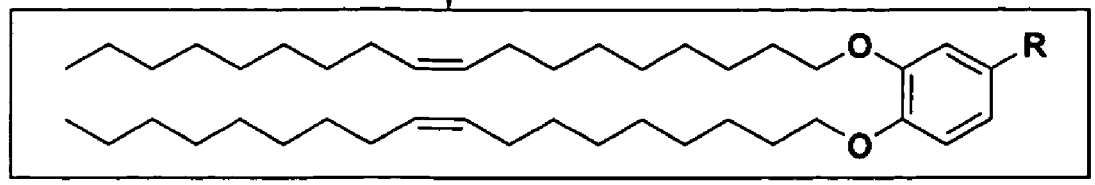
FIG. 7 depicts scheme 5, a final step in the present invention to produce the desired lipid-polyamine conjugates by acidification of the amines with a solution of anhydrous HCl in ethyl acetate.
Figure 7:
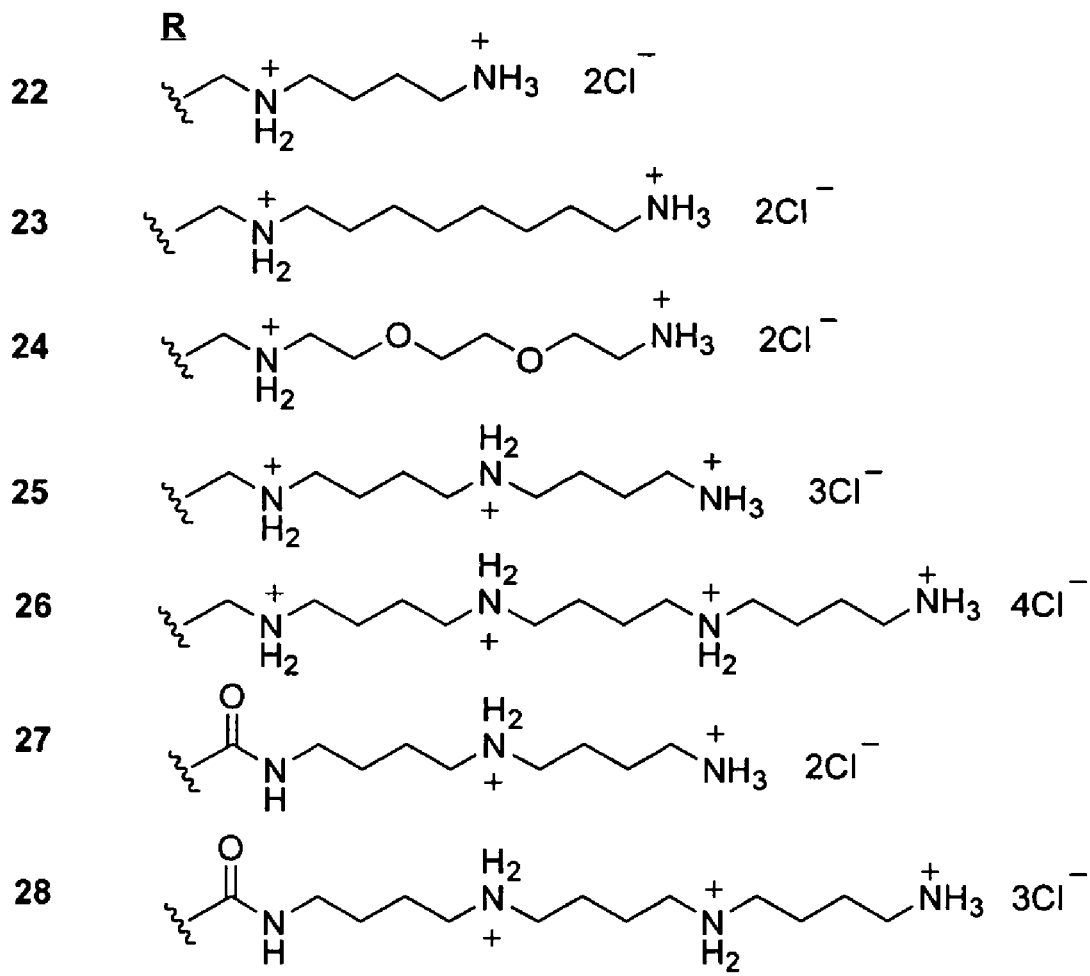

The final step to produce the desired lipid-polyamine conjugates involved acidification of the amines with a solution of anhydrous HCl in ethyl acetate.[23,24] As shown in Scheme 5 (shown in FIG. 7), treatment of the penultimate compounds 15-21 with anhydrous HCl/EtOAc provided the target HCl salts, 22-28. By design, the lipid portion of the conjugate (boxed structure in Scheme 5) was held constant throughout the series. This feature allowed for later comparisons and an understanding of how the polyamine component influenced DNA delivery.

Biological Evaluation.

Before conducting the transfection studies, the series of conjugates (22-28) were first evaluated for cytotoxicity in Chinese Hamster Ovary (CHO) cells. This was an important step in determining what dose of lipid-polyamine conjugate could be tolerated by the cell line. Ideally, one would use a dose of the conjugate, which is not cytotoxic to the cell line to be transfected. This is an important caveat in evaluating DNA delivery systems.

As expected, there were significant differences in the aqueous solubility of these new conjugates. DMSO was added in portions to provide aqueous solutions of 22-28. Since DMSO itself is toxic to CHO cells above 40 µM, stock solutions of each conjugate were made in such a manner so that the total DMSO concentration remained below 40 µM. This constraint limited the amount of conjugate that could be dosed. Poorly-soluble materials required higher DMSO levels, which in turn limited the amount of material that could be dosed to cells in our toxicity screen.

Taking these factors into account, cytotoxicity screens were performed to investigate the relative toxicity of each system. Most materials were relatively non-toxic with $IC_{50}$ values $\geq 20$ µM. Armed with this insight, cells were treated with $\leq 6.4$ µM of the polyamine conjugate so as to avoid significant toxic effects from the delivery agent itself. Indeed, at this dose $\geq 90\%$ of cells survived transfection for all compounds except 28. Indeed, compound 28 was very toxic (after 24 h incubation) and even at the lowest dose used for transfection (0.5 µg/mL; 0.5 µM 28) killed 95% of the cells. As such, 28 was too toxic for efficient transfection at the doses surveyed and its data is strongly biased by the few remaining cells, which survived.

Gene Transfer Studies.

Figure 8:
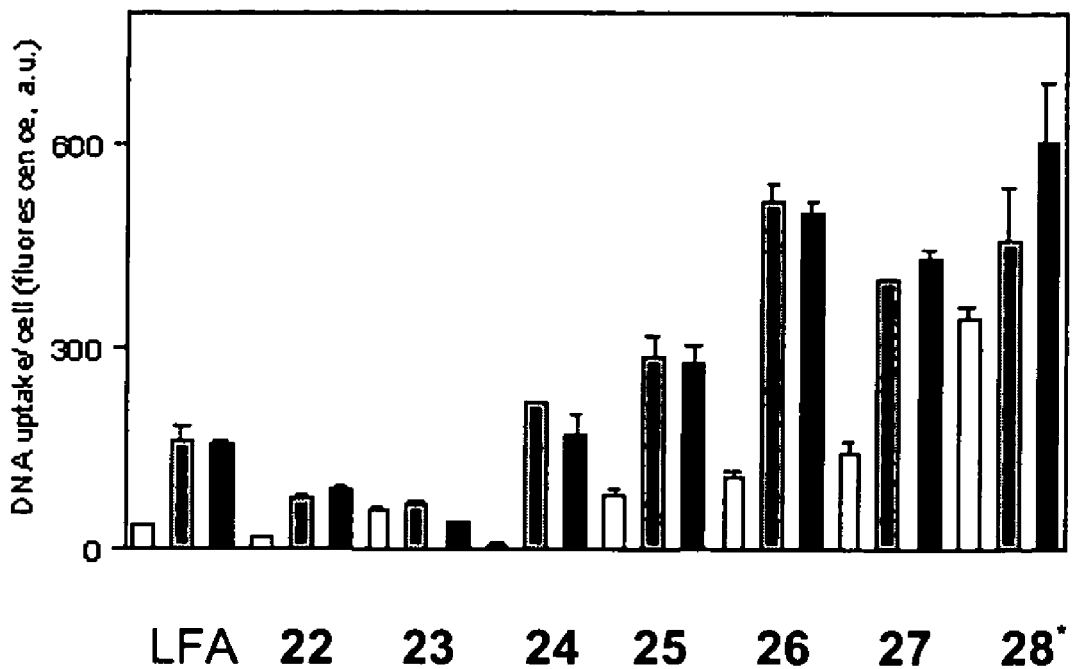
FIG. 8 shows DNA uptake activity by novel cationic lipids 22-28 (compared with Lipofectamine, LFA). CHO K1 cells were grown to confluence in 24-well plates, rinsed with medium and incubated for 4 h at 37° C. with 1 µg/mL Alexa Fluor-488-DNA complexed with 0.5 µg/mL (white bars), 2.5 µg/mL (gray bars), or 5 µg/mL (black bars) of the respective cationic lipid, as indicated above each entry; cells were then extensively washed with PBS, treated with trypsin, and cell pellets were again extensively washed with PBS 1% BSA to completely remove non-specific fluorescence from the cell exterior; finally, cells were analyzed for Alexa Fluor-488-DNA uptake by flow cytometry on a FACSCalibur (BD Biosciences) operated by Cell-Quest software. (*) during this relatively short incubation (4 h), cells remained viable with 28; note: in converting from µg/mL to µM, the concentrations used were typically approximately 0.6, 3.0, and 6 µM, respectively.

Armed with knowledge of the cytotoxicity range of the series 22-28, CHO-K1 cells were evaluated for DNA uptake using a fluorescently labeled DNA Alexa Fluor-488-DNA). As shown in FIG. 8, cells were dosed with the Alexa Fluor-488-DNA in the presence of increasing concentrations (i.e., 0.5, 2.5, 5 µg/mL) of the respective conjugate, 22-28. Each conjugate was as good (24, 25) or better (26, 27) than the lipofectamine control (LFA, except 22 and 23) and facilitated uptake of the fluorescent DNA probe in a concentration-dependent manner (µg/mL).

While the molecular weights in this series do range from 784 (22), 840 (23), 844 (24), 891 (25), 999 (26), 869 (27), and 976 g/mol (28), they are relatively close (within 10-22%) and allow for general comparisons, especially in light of the large differences observed in activity. For example, tetraamine 26, which has the highest molecular weight of the series (999 g/mol), was at a slightly lower concentration (5 µM) than 22 (6.4 µM) at the 5 µg/mL dose. Nevertheless, DNA uptake experiments with tetraamine 26 had over a 5-fold increase in DNA uptake (as measured by fluorescence of the imported DNA probe) than those conducted with diamine 22. Clearly, compound 26 was more efficient in facilitating DNA delivery to cells.

Interestingly, conjugate 27, which represents a butanediamine motif similar to 22 except with the diamine placed further away from the lipid tail, was a more efficient DNA delivery agent than 22. In contrast, compound 23, which separated the ammonium centers via an octanediamine had similar or lower activity as 22 (depending on the dose). Insertion of the polyether motif present in 24 maintained this eight-atom spacer, yet nearly doubled the DNA delivery (DNA probe fluorescence) observed.

The PAT-selective homospermidine motif present in 25 resulted in a three-fold increase in DNA delivery. However, this outcome may simply be due to the presence of the additional charge provided by the triamine motif present in 25. Indeed, significant increases in DNA delivery were observed across the homologous series 22, 25, and 26 which at 5 μg/mL gave 94, 281 and 504 fluorescence absorbance units (a.u.), respectively.

FIG. 8. shows DNA uptake activity by novel cationic lipids 22-28 (compared with Lipofectamine, LFA). CHO K1 cells were grown to confluence in 24-well plates, rinsed with medium and incubated for 4 h at 37° C. with 1 μg/mL Alexa Fluor-488-DNA complexed with 0.5 μg/mL (white bars), 2.5 μg/mL (grey bars), or 5 μg/mL (black bars) of the respective cationic lipid, as indicated above each entry. Cells were then extensively washed with PBS, treated with trypsin, and cell pellets were again extensively washed with PBS 1% BSA to completely remove non-specific fluorescence from the cell exterior. Finally, cells were analyzed for Alexa Fluor-488-DNA uptake by flow cytometry on a FACSCalibur (BD Biosciences) operated by Cell-Quest software. (*) during this relatively short incubation (4 h), cells remained viable with 28. Note: in converting from μg/mL to μM, the concentrations used were typically approximately 0.6, 3.0, and 6 μM, respectively and are tabulated specifically in the Supporting information.

Figure 9:
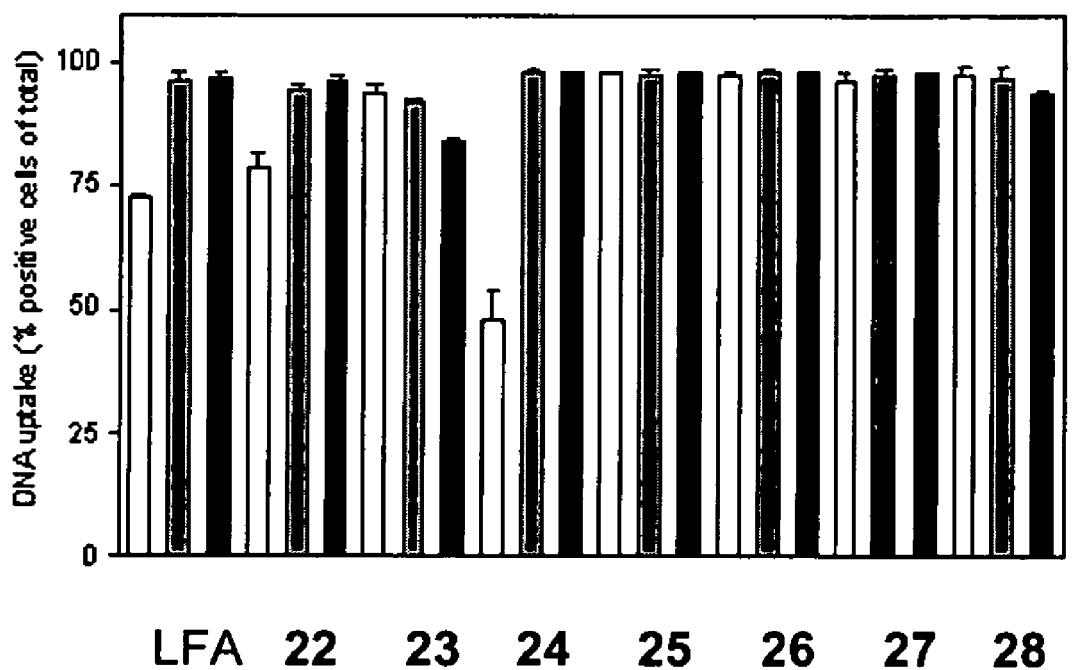
FIG. 9 shows the results obtained from the experiment described by FIG. 8, which were analyzed using a gated channel to determine the percentage of cells that had internalized significant amounts of DNA as compared with cells incubated with DNA only; a gate was set just above the threshold signal for control cells (DNA only with no lipid conjugate); note: Alexa Fluor-488-DNA complexed with 0.5 µg/mL (white bars), 2.5 µg/mL (gray bars), or 5 µg/mL (black bars) of the respective cationic lipid was used, as indicated in FIG. 8; data are presented as the mean±SD.

In FIG. 9 we see the results obtained from the experiment described by FIG. 8, which were analyzed using a gated channel to determine the percentage of cells that had internalized significant amounts of DNA as compared with cells incubated with DNA only. A gate was set just above the threshold signal for control cells (DNA only with no lipid conjugate). Note: Alexa Fluor-488-DNA complexed with 0.5 μg/mL (white bars), 2.5 μg/mL (grey bars), or 5 μg/mL (black bars) of the respective cationic lipid was used, as indicated in FIG. 8. Data are presented as the mean±SD.

While the average amount of DNA taken up/cell shows wide variations between the different compounds (FIG. 8), all compounds were able to deliver significant amounts of DNA to virtually the entire cell population (FIG. 9). However, in terms of gene therapy, simple DNA delivery to the cell is insufficient. There are other cellular barriers, which must be traversed.

GFP Expression Studies.

In order for the 'therapy' to be effective, the DNA must escape from the endosome and enter the cell's nucleus, be transcribed to a regulatory, non coding RNA (RNAi) or to mRNA that is translated into its coded protein. Therefore, we investigated the conjugate-assisted expression of an eGFP DNA plasmid encoding for the green fluorescent protein (GFP). CHO cells, which were successfully transfected, were easily identified by their green fluorescence. Control experiments conducted with only the eGFP DNA plasmid (and no lipid carrier) gave virtually no fluorescence. A gate or instrumental threshold was set based upon this low background fluorescence. Fluorescence detected above this background was considered a positive response.

Figure 10:
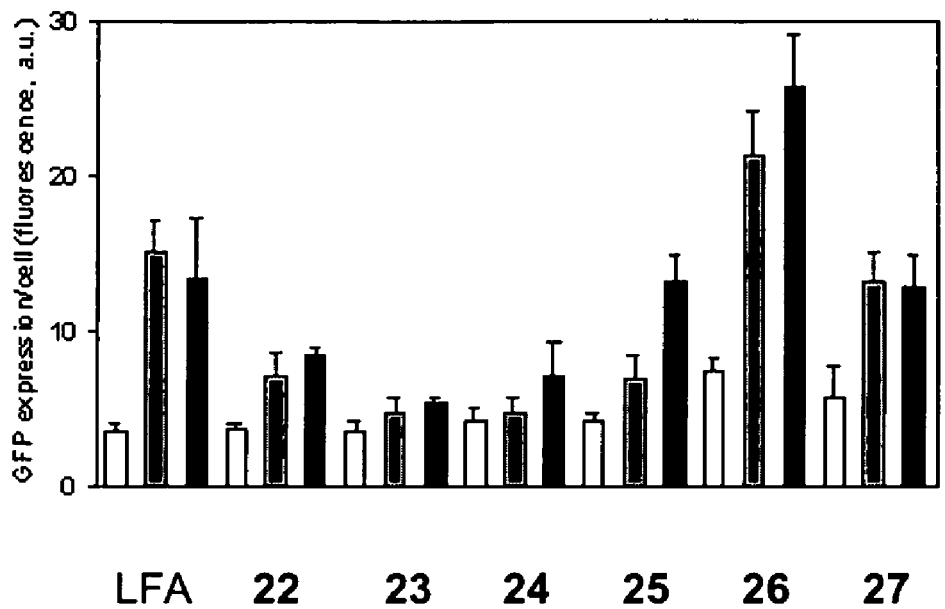
FIG. 10 illustrates GFP expression results from transfection experiments; CHO K1 cells were grown to approximately 50% sub-confluence in 24-well plates, rinsed with medium and incubated for 4 h at 37° C. with 1 µg/mL eGFP DNA plasmid complexed with 0.5 µg/mL (white bars), 2.5 g/mL (gray bars), or 5 µg/mL (black bars) of the respective cationic lipid, as indicated above. Medium was then changed, and cells were incubated for another 24 h to allow for GFP plasmid expression; cells were detached by trypsin treatment and analyzed for GFP expression by FACS; Lipofectamine is denoted as LFA; the value obtained with DNA plasmid only was subtracted from each entry above (almost negligible)

FIG. 10. GFP Expression Results from Transfection Experiments.

CHO K1 cells were grown to approx. 50% sub-confluence in 24-well plates, rinsed with medium and incubated for 4 h at 37° C. with 1 μg/mL eGFP DNA plasmid complexed with 0.5 μg/mL (white bars), 2.5 μg/mL (grey bars), or 5 μg/mL (black bars) of the respective cationic lipid, as indicated above. Medium was then changed, and cells were incubated for another 24 h to allow for GFP plasmid expression. Cells were detached by trypsin treatment and analyzed for GFP expression by FACS. Lipofectamine is denoted as LFA. The value obtained with DNA plasmid only was subtracted from each entry above (almost negligible).

The results obtained from the experiment described in FIG. 10 were analyzed using a gated channel to determine the percentage of cells that expressed significant levels of GFP as compared with cells incubated with DNA plasmid only. A gate was set just above the threshold measured with no DNA plasmid and no conjugate added (almost negligible). All cells which exhibited a fluorescence signal above that level were considered positive. Data are presented as the mean±SD. These are shown in FIG. 11.

Figure 11:
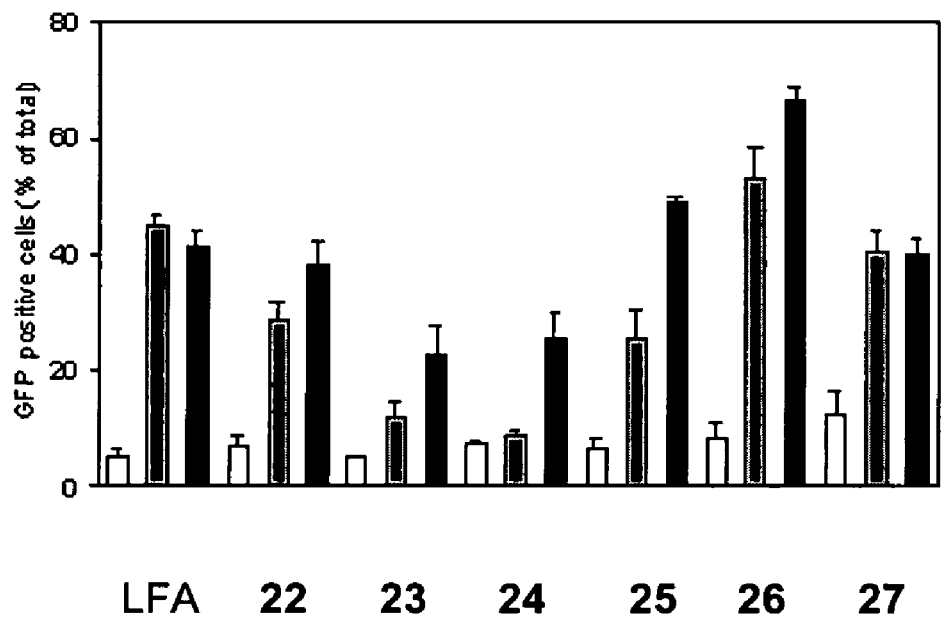
FIG. 11 shows the results obtained from the experiment described in FIG. 10, which were analyzed using a gated channel to determine the percentage of cells that expressed significant levels of GFP as compared with cells incubated with DNA plasmid only; a gate was set just above the threshold measured with no DNA plasmid and no conjugate added (almost negligible); all cells which exhibited a fluorescence signal above that level were considered positive; data are presented as the mean±SD.

The interpretation of the data in FIGS. 10 and 11 can be quite subtle. For example, FIG. 10 relates the amount of GFP expression per cell and is a summary measurement of how well the DNA 'message' was delivered, read and protein (GFP) produced. While the magnitudes are different the relative trends are consistent with those observed in FIG. 8. In this regard, DNA delivery correlated with GFP expression.

FIG. 11 revealed the % GFP positive cells observed in the total cell population after the transfection experiment. This information is a direct measure of transfection efficiency. Using the 5 μg/mL dose for comparisons, 22 (38%), 25 (49%), and 27 (40%) were all comparable to the LFA control (41%) in terms of transfection efficiency. Both 23 (23%) and 24 (25%) gave lower values. The lone standout was tetraamine 26 (67%), which had over 50% higher transfection efficiency than the LFA control (41%).

Cells treated with conjugate 23 at the high dose (5 μg/mL, black bars in FIG. 9) gave 84% positive cells of the total cell population remaining after the DNA uptake experiment; whereas all the others (LFA, 22, and 24-28) gave typically >94% positive cells. Using these data as benchmarks of DNA import via each conjugate, the significantly lower % GFP positive cells (23-67%) observed in FIG. 11 suggests that intracellular processing and nuclear delivery of DNA also depend on the structure of the cationic lipid.

A closer analysis of the data revealed just how important these latter two parameters (i.e., intracellular processing and nuclear delivery) are for successful gene delivery. For example, although 26 was capable of delivering 3-fold more DNA to the cell than the control LFA (black bars in FIG. 8: 26: 504; LFA: 158 a.u.), the relative GFP expression/cell was only two fold higher in FIG. 10 (25 vs. 13 a.u.) and the % of GFP positive cells was only 1.5 fold higher in FIG. 11 (67% vs. 41%).

It cannot be excluded that maximum GFP expression occurs at varying time points post-transfection for the different compounds. Nevertheless, the data reflect an interesting correlation between intracellular processing of internalized DNA and the cationic lipid structure.

In summary, while a significant number of cells imported the fluorescent DNA probe in the presence of the synthetic conjugates (22-28), the amount of the DNA probe entering each cell varied depending upon the conjugate used. The % GFP positive cells of the total cell population roughly correlated with the GFP expression/cell. Cells with low % GFP positive cells (FIG. 11: 23, 23%; 24, 25%) had low GFP expression/cell (FIG. 10: 23, 5; 24, 7). Cells with high % GFP positive cells (FIG. 11: 26, 67%) had high GFP expression/cell (FIG. 10: 26, 25). Indeed, the additional 'intracellular barriers' associated with successful GFP expression (as shown in FIG. 11 in terms of % GFP positive cells) seemed to moderate the large differences seen in the earlier DNA delivery study (FIG. 8).

Figure 12:
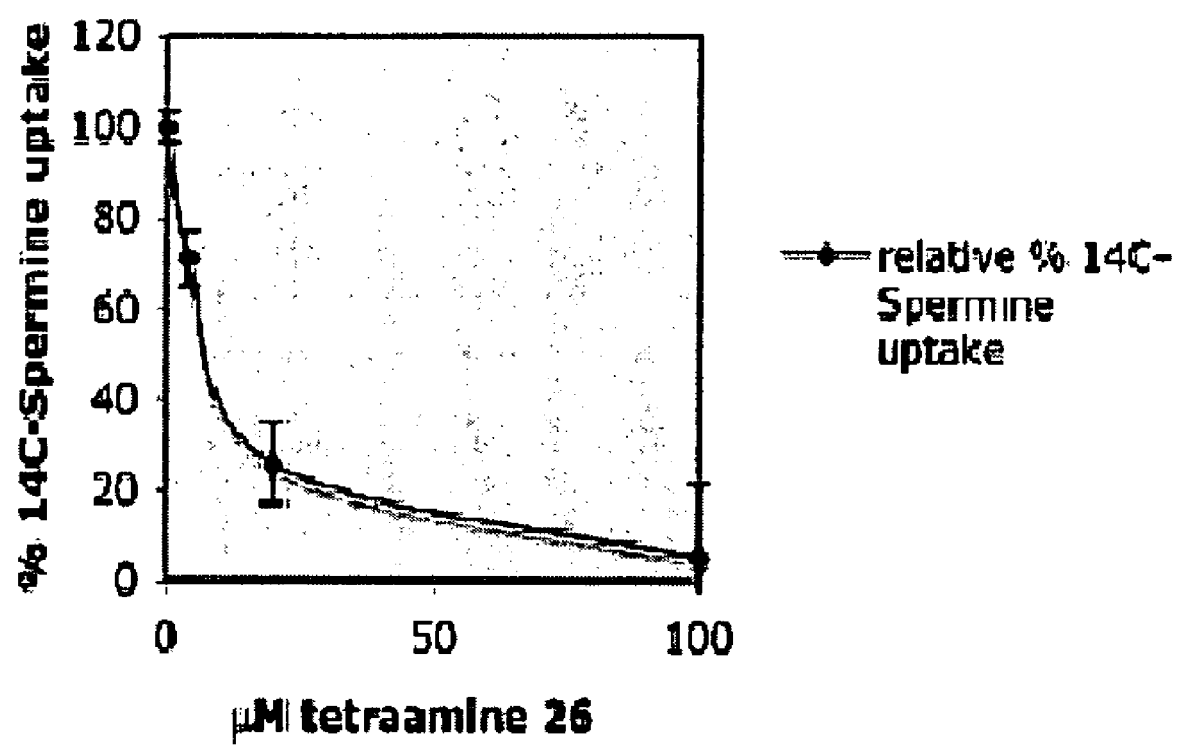
FIG. 12 shows [$^{14}$C]Spermine uptake inhibition by 26; tetraamine 26 is an efficient inhibitor of polyamine uptake; CHO-K1 cells were incubated with 1 µM [$^{14}$C]spermine (31 Ci/mol) for 20 min in serum free medium supplemented with varying concentrations of tetraamine 26 as indicated in the figure; after extensive rinsing, imported [$^{14}$C]spermine was determined by scintillation counting on cell lysates.

We theorized that 26 may be using the polyamine transporter, PAT, for cellular entry. Indeed, as shown in FIG. 12, tetraamine 26 was shown to be a potent inhibitor of spermine uptake ($IC_{50}$ of approximately 10 μM) using a $^{14}C$-radiolabeled spermine competition assay. This observation implied that 26 was able to compete for the polyamine recognition sites on the cell surface (e.g., PAT). Therefore, it is possible that certain lipophilic polyamines, which present the correct polyamine 'message', may be able to recognize and target cells expressing high levels of polyamine transporters on their cell surface (e.g., cancer cells, rapidly dividing tumors, etc.). However, as shown in this report, delivery into the cell is just one step in successful gene transfection. Nevertheless, the findings disclosed herein are an important first step in developing 'smart' transfection agents.

Proof-of-principle for this novel therapeutic approach was provided in the following journal article which utilized an anti-cancer toxin that consisted of a chemical conjugate between the human urokinase plasminogen activator and saporin: Lipopolyamine Treatment Increases the Efficacy of Intoxication with Saporin and an Anticancer Saporin Conjugate. Geden S. E.; Gardner R. A.; Fabbrini M. S.; Ohashi M.; Phanstiel, IV, O.; Teter K. *FEBS J.* 2007, 274, 4825-4836 (published online Aug. 22, 2007). This journal article is incorporated herein by reference in its entirety.

We have also documented lipopolyamine-induced toxin sensitization with two other saporin-based toxins: (i) FGF-saporin, a chemical conjugate between fibroblast growth factor and saporin; and (ii) the OKT10 immunotoxin which consists of a chemical conjugate between saporin and an antibody that recognizes the CD38 cancer antigen. DU145 human prostate cancer cells exposed to lipopolyamine 26 and FGF-saporin were 85-fold more sensitive to intoxication than cells incubated with FGF-saporin alone. The commercial transfection agent Lipofectamine generated significant cellular sensitization to FGF-saporin as well. However, Lipofectamine also sensitized a non-target cell population (HeLa cells, which do not express the FGF receptor) to FGF-saporin. In contrast, HeLa cells exposed to lipopolyamine 26 and FGF-saporin were no more sensitive to intoxication than cells incubated with FGF-saporin alone. Our reagent thus exhibited a level of specificity that was not seen with Lipofectamine. We have also shown that Ramos human leukemia cells exposed to lipopolyamine 26 and OKT10 are 100-fold more sensitive to intoxication than cells incubated with OKT10 alone. Ramos cells exposed to Lipofectamine and OKT10 were no more sensitive to intoxication than cells exposed to OKT10 alone. Collectively, these results demonstrate the utility of our lipopolyamine compounds over the commercially available Lipofectamine reagent.

Conclusions.

This investigation demonstrated that the number and position of the positive charges along the polyamine scaffold plays a key role in DNA delivery and in determining the intracellular outcome of the DNA import event, i.e. the transfection efficiency. Although the Lipofectamine (LFA: 75% 4 and 25% 6 mixture) has five positive charges (presumably a DNA delivery enhancing feature) in one of its components (e.g., 4), it also has a neutral component DOPE 6 present, which makes structural comparisons to this control difficult beyond the dose to dose comparisons made above. Future studies will look at the effect of neutral lipids (like 6) in terms of transfection efficiency of polyamine-lipid conjugates. Indeed, DOPE 6 has been shown to play a role in endosome disruption and to facilitate transfection.[35]

In addition, this paper presented the first study, which probed the transfection phenomena with a PAT-selective homospermidine motif[28] attached to a lipid cargo, e.g., 25. As expected compound 25 showed a 3-fold enhancement in DNA delivery over its butanediamine analogue 22. Unfortunately, the DNA delivery enhancement observed with 25 seemed to be muted by the latter steps of the transfection process (e.g., intracellular trafficking, nuclear delivery, etc). As a result, 25 had only slightly higher transfection efficiency than 22 (e.g., 25 and 22 gave 49% and 38% GFP positive cells in FIG. 11, respectively).

This phenomenon was also observed with the two diamines, 27 and 22. Compound 27 showed greater than 4-fold enhancement in DNA delivery over its butanediamine analogue 22. Evidently, moving the diamine 'message' further away from the lipid component enhanced the delivery characteristics of the conjugate (FIG. 8). Again, this potential delivery enhancement by 27 was tempered by the latter steps of the transfection process. Alas, nearly identical transfection efficiency was observed for 27 and 22 (40% and 38% GFP positive cells in FIG. 11, respectively).

Clearly, cellular DNA delivery alone is insufficient for successful transfection. Understanding how different polyamine structures[21,36] and neutral lipids like 6[35] enhance the intracellular trafficking and nuclear delivery of plasmid DNA is critical for the future design of efficient polyamine transfection agents.

Experimental.

Materials.

Silica gel (32-63 μm) and chemical reagents were purchased from commercial sources and used without further purification. All solvents were distilled prior to use. $^1$H and $^{13}$C NMR spectra were recorded at 300 and 75 MHz, respectively, unless otherwise noted. TLC solvent systems are based on volume % and NH$_4$OH refers to concentrated aqueous NH$_4$OH. High-resolution mass spectrometry was performed at the University of Florida Mass Spectrometry facility.

Materials and Methods

ULYSIS AlexaFluor-488 (Molecular Probes) was used for labeling of DNA as recommended by the manufacturer. All fine chemicals were from Sigma. Lipofectamine 2000 was purchased from Invitrogen. Wild-type Chinese hamster ovary cells (CHO-K1) were obtained from the ATCC (Manassas, Va., USA). CHO cells were routinely cultured in F12K nutrient mixture supplemented with 10% (v/v) fetal calf serum, 2 mM L-glutamine, 100 units/ml penicillin, and 100 μg/ml streptomycin (growth medium) in a humidified 5% CO$_2$, 37° C. incubator.

DNA uptake studies. AlexaFluor-488 labeled DNA with or without cationic lipid was mixed in serum-free F12K and added to extensively rinsed cells grown in 24-well plates. Cells were then incubated for 4 h at 37° C. After removal of the incubation medium and rinsing with PBS, cells were detached with trypsin followed by extensive washing with ice-cold PBS, 1% (w/v) bovine serum albumin (BSA) to remove non-specific fluorescence. Finally, cells were suspended in PBS, 1% BSA and analyzed for DNA uptake by flow cytometry on a FACSCalibur (BD Biosciences) operated by Cell-Quest software. Cells remained viable with all compounds tested, including 28.

GFP transfection experiments—eGFP encoding DNA plasmid with or without cationic lipid was mixed in F12K and incubated with pre-rinsed, sub-confluent cells in 24-well plates for 4 h, followed by another incubation period of 24 h in growth medium. Cells were then washed with PBS, detached by trypsin treatment, dissolved in PBS, 1% BSA, and analyzed by FACS for GFP expression. Note: severe toxicity was noted for compound 28 after the 24 h incubation period.

Biological Studies.

CHO cells were grown in RPMI medium supplemented with 10% fetal calf serum, glutamine (2 mM), penicillin (100 U/mL), streptomycin (50 μg/mL). Cells were grown at 37° C. under a humidified 5% CO$_2$ atmosphere. Aminoguanidine (2 mM) was added to the culture medium to prevent oxidation of the drugs by the enzyme (bovine serum amine oxidase) present in calf serum. Trypan blue staining was used to determine cell viability before the initiation of a cytotoxicity experiment. L1210 cells in early to mid log-phase were used. Cell growth was assayed in sterile 96-well microtiter plates (Becton-Dickinson, Oxnard, Calif., USA). CHO cells were plated at $2e^3$ cells/mL. Drug solutions (10 µL per well) of appropriate concentration were added after an overnight incubation for the CHO cells. After exposure to the drug for 48 hr, cell growth was determined by measuring formazan formation from 3-(4,5-dimethylthiazol-2-yl)2,5-diphenyltetrazolium using a Titertek Multiskan MCC/340 microplate reader for absorbance (540 nm) measurements.[37] These experiments allowed for a quick assessment of conjugate cytotoxicity and facilitated determination of the proper dosing for the latter transfection and delivery experiments.

3,4-Bis-octadec-9-enyloxy-benzaldehyde (8a):

To a solution of oleyl bromide (1.8 g, 5.4 mmol) in cyclohexanone (20 ml) was added protocatachualdehyde (0.341 g, 2.5 mmol), potassium carbonate (1.02 g, 7.4 mmol) and potassium iodide (0.05 g, 0.3 mmol). The suspension was stirred at 100° C. for 18 hours under nitrogen. Due to the light sensitivity of the oleyl bromide the flask was covered in aluminum foil. TLC (10% MeOH/CHCl$_3$) showed the reaction was complete. The hot reaction mixture was filtered to remove some of the particulates and the solvent was removed in vacuo. The residue was dissolved in CHCl$_3$ (100 mL) and washed with water (2×75 mL). The CHCl$_3$ layer was dried over anhydrous sodium sulphate, filtered and the solvent removed in vacuo to give a dark yellow oil. The oily residue was purified by flash column chromatography (5% EtAc/hexane) to yield the product 8a as a white solid (1.08 g, 69%), $R_f$=0.3 (5% EtAc/hexane). $^1$H NMR (CDCl$_3$) d 9.80 (s, 1H, CHO), 7.37 (m, 2H, phenyl), 6.93 (d, 1H, phenyl), 5.33 (t, 4H, olefinic), 4.06 (t, 2H, OCH$_2$), 4.04 (t, 2H, OCH$_2$), 2.01 (m, 8H, CH$_2$C=C), 1.85 (m, 4H, CH$_2$CH$_2$O), 1.50-1.18 (m, 44H, 22×CH$_2$), 0.88 (t, 6H, CH$_3$); $^{13}$C NMR (CDCl$_3$) d 191.00, 155.34, 149.95, 130.14, 130.12, 129.97, 126.79, 111.89, 111.04, 69.36, 32.29, 30.16, 29.92, 29.90, 29.88, 29.72, 29.64, 29.62, 29.44, 29.36, 27.60, 26.37, 26.34, 23.09, 14.53; HRMS (FAB): theory for C$_{43}$H$_{75}$O$_3$ (M+1), 639.5716; found (M+1), 639.5755. Anal. (C$_{43}$H$_{74}$O$_3$): C, H.

3,4-Bis-octadec-9-enyloxy-benzoic acid (8c):

To a solution of oleyl bromide (1.8 g, 5.4 mmol) in cyclohexanone (20 ml) was added ethyl 3,4-dihydroxybenzoate 7b (0.45 g, 2.5 mmol), potassium carbonate (1.02 g, 7.4 mmol) and potassium iodide (0.05 g, 0.3 mmol). The suspension was stirred at 100° C. for 18 hours under nitrogen. Due to the light sensitivity of the oleyl bromide the flask was covered in aluminum foil. The hot reaction mixture was filtered to remove some of the particulates and the solvent was removed in vacuo. The residue containing ester 8b was dissolved in a solution of ethanol (20 mL) containing potassium hydroxide (0.8 g, 20 mmol) and refluxed for 4 h. The hot reaction mixture was added to water (30 mL) and acidifying with 1M HCl to pH 1 resulted in the precipitation of a white solid. The solid 8c was filtered off and washed several times with water. The crude acid was re-crystallized from ethanol (10 mL) to give the product 8c as a white solid (1.14 g, 70%); $^1$H NMR (500 MHz, CDCl$_3$) d 7.73 (dd, 1H, phenyl), 7.58 (d, 1H, phenyl), 6.89 (d, 1H, phenyl), 5.35 (t, 4H, olefinic), 4.05 (2×t, 4H, 2×OCH$_2$), 2.01 (m, 8H, CH$_2$=C), 1.85 (m, 4H, C H$_2$CH$_2$O), 1.48 (quin, 4H, 2×CH$_2$), 1.41-1.19 (m, 40H, 20×CH$_2$), 0.88 (t, 6H, CH$_3$).

Acid chloride (8d):

See Compound 20 for experimental details.

(4-Amino-butyl)-carbamic acid tert-butyl ester (9):

1,4-Diaminobutane (4.4 g, 0.05 mol) was dissolved in a solution of triethylamine and methanol (10% TEA in MeOH, 110 mL). A solution of di-tert-butyl dicarbonate (3.63 g, 0.017 mol) in methanol (10 mL) was added dropwise to this mixture with vigorous stirring. The mixture was stirred at RT overnight. The tert-butoxy-carbonylation was complete as evidenced by TLC (4% NH$_4$OH/MeOH). The excess 1,4-diaminobutane, methanol and TEA were removed in vacuo to yield an oily residue that was dissolved in dichloromethane (100 mL) and washed with a solution of sodium carbonate (10% aq, 2×100 mL). The organic layer was dried over anhydrous sodium sulfate, filtered, the solvent removed in vacuo and the oily residue purified by flash column chromatography (1:10:89 NH$_4$OH:MeOH:CHCl$_3$) to give the product 9 as a clear oil (2.23 g, 71%), $R_f$=0.38 (1:10:89 NH$_4$OH:MeOH:CHCl$_3$). $^1$H NMR (CDCl$_3$) d 4.72 (br s, 1H, NHCO), 3.12 (q, 2H, CH$_2$), 2.70 (t, 2H, CH$_2$), 1.57-1.30 (m, 13H, 2×CH$_2$, 3×CH$_3$).

[4-(3-Cyano-propylamino)-butyl]-carbamic acid tert-butyl ester (10):

To a solution of the BOC protected diamine 9 (2.10 g, 0.01 mol) in anhydrous acetonitrile (50 mL) was added potassium carbonate (5.14 g) and the suspension was stirred at RT for 10 minutes. A solution of 4-bromobutyronitrile (1.65 g, 0.01 mol) in acetonitrile (25 mL) was added and the resulting mixture stirred at 50° C. for 24 hours. TLC (1:10:89 NH$_4$OH:MeOH:CHCl$_3$) showed that the reaction was 95% complete. The mixture was filtered to remove most of the inorganic salts and the acetonitrile was removed in vacuo to give a solid/oily residue that was purified by flash column chromatography (1:5:94 NH$_4$OH:MeOH:CHCl$_3$) to yield the product 10 as a clear oil (1.74 g, 61%), $R_f$=0.5 (1:10:89 NH$_4$OH:MeOH:CHCl$_3$); $^1$H NMR (CDCl$_3$) d 4.79 (br s, 1H, NHCO), 3.12 (q, 2H, CH$_2$), 2.74 (t, 2H, CH$_2$), 2.60 (t, 2H, CH$_2$), 2.46 (t, 2H, CH$_2$), 1.81 (quin, 2H, CH$_2$) 1.57-1.37 (m, 13H, 2×CH$_2$, 3×CH$_3$).

(4-tert-Butoxycarbonylamino-butyl)-(3-cyano-propyl)-carbamic acid tert-butyl ester (11):

The amino-nitrile 10 (1.74 g, 6.8 mmol) was dissolved in a solution of triethylamine and methanol (10% TEA in MeOH, 40 mL). A solution of di-tert-butyl dicarbonate (3.63 g, 0.017 mol) in methanol (20 mL) was added dropwise to this mixture with vigorous stirring. The mixture was stirred at it overnight. TLC (1:10:89 NH$_4$OH:MeOH:CHCl$_3$) showed the tert-butoxycarbonylation was complete. The methanol and TEA were removed in vacuo to yield an oily residue that was dissolved in dichloromethane (100 mL) and washed with a solution of sodium hydroxide (2.5 M, 3×30 mL) and water (2×30 mL). The organic layer was dried over anhydrous Na$_2$SO$_4$, filtered, the solvent removed in vacuo and the oily residue purified by flash column chromatography (40% EtAc/hexane) to give the product 11 as a clear oil (2.10 g, 87%), $R_f$=0.45 (40% EtAc/hexane); $^1$H NMR (CDCl$_3$) d 4.60 (br s, 1H, NHCO), 3.28 (t, 2H, CH$_2$), 3.14 (m, 4H, 2×CH$_2$), 2.35 (t, 2H, CH$_2$), 1.88 (quin, 2H, CH$_2$), 1.58-1.28 (m, 22H, 2×CH$_2$, 6×CH$_3$).

(4-Amino-butyl)-(4-tert-butoxycarbonylamino-butyl)-carbamic acid tert-butyl ester (12):

The nitrile 11 (2.00 g, 5.6 mmol) was dissolved in ethanol (100 mL). NH$_4$OH (10 mL) and Raney nickel (8 g) were added and ammonia gas was bubbled through the solution for 20 minutes at 0° C. The suspension was hydrogenated at 50 parr for 24 hours. Air was bubbled through the solution and the Raney nickel was removed by filtering through a sintered glass funnel keeping the Raney nickel residue moist at all times. The ethanol and NH$_4$OH were removed in vacuo and the oily residue dissolved in CH$_2$Cl$_2$ and washed with 10% aq, Na$_2$CO$_3$ (3×50 mL). The organic layer was dried over anhydrous Na$_2$SO$_4$, filtered and the solvent removed in vacuo to give the product 12 as a clear oil without further purification (1.92 g, 95%), R$_f$=0.4 (1:10:89 NH$_4$OH:MeOH:CHCl$_3$); $^1$H NMR (CDCl$_3$) d 4.65 (br s, 1H, NHCO), 3.14 (m, 6H, 3×CH$_2$), 2.69 (t, 2H, CH$_2$), 2.35 (t, 2H, CH$_2$), 1.58-1.26 (m, 26H, 4×CH$_2$, 6×CH$_3$).

(4-tert-Butoxycarbonylamino-butyl)-{4-[tert-butoxycarbonyl-(3-cyano-propyl)-amino]-butyl}-carbamic acid tert-butyl ester (13):

To a solution the amine 12 (1.32 g, 3.68 mmol) in anhydrous acetonitrile (20 mL) was added potassium carbonate (1.7 g) and the suspension was stirred at rt for 10 minutes. A solution of 4-bromobutyronitrile (0.54 g, 3.68 mmol) in acetonitrile (10 mL) was added and the resulting mixture stirred at 50° C. under nitrogen for 24 hours. TLC (1:10:89 NH$_4$OH:MeOH:CHCl$_3$) showed the reaction was 95% complete. The mixture was filtered to remove most of the inorganic salts and the acetonitrile was removed in vacuo to give a solid/oily residue. The oil was dissolved in anhydrous THF (70 mL). A solution of di-tert-butyl dicarbonate (1.21 g, 5.5 mmol) in THF (20 mL) was added dropwise to this mixture with vigorous stirring. The mixture was stirred at RT overnight. TLC (1:10:89 NH$_4$OH:MeOH:CHCl$_3$) showed the tert-butoxycarbonylation was complete. The THF was removed in vacuo to yield an oily residue that was dissolved in dichloromethane (100 mL) and washed with a solution of sodium hydroxide (2.5 M, 3×30 mL). The organic layer was dried over anhydrous sodium sulfate, filtered, the solvent removed in vacuo and the oily residue purified by flash column chromatography (CHCl$_3$/MeOH 99:1) to give the product 13 as a clear oil (1.46 g, 75%), R$_f$=0.5 (CHCl$_3$/MeOH 99:2); $^1$H NMR (CDCl$_3$) d 4.63 (bs, 1H, NHCO), 3.28 (t, 2H, CH$_2$), 3.14 (m, 8H, 4×CH$_2$), 2.64 (t, 2H, CH$_2$), 1.88 (quin, 2H, CH$_2$), 1.58-1.35 (m, 35H, 4×CH$_2$, 9×CH$_3$).

{4-[(4-Amino-butyl)-tert-butoxycarbonyl-amino]-butyl}-(4-tert-butoxycarbonyl-amino-butyl)-carbamic acid tert-butyl ester (14):

The nitrile 13 (1.33 g, 2.5 mmol) was dissolved in ethanol (100 mL). NH$_4$OH (10 mL) and Raney nickel (6 g) were added and ammonia gas was bubbled through the solution for 20 minutes at 0° C. The suspension was hydrogenated at 50 psi for 24 hours. Air was bubbled through the solution and the Raney nickel was removed by filtering through a sintered glass funnel keeping the Raney nickel residue moist at all times. The ethanol and NH$_4$OH were removed in vacuo and the oily residue dissolved in CH$_2$Cl$_2$ and washed with sodium carbonate (10%, aq, 3×50 mL). The organic layer was dried over anhydrous sodium sulphate, filtered and the solvent removed in vacuo. The oil was purified by flash column chromatography (1:10:89 NH$_4$OH:MeOH:CHCl$_3$) to give the product 14 as a clear oil (0.85 g, 64%), R$_f$=0.5 (1:10:89 NH$_4$OH:MeOH:CHCl$_3$). $^1$H NMR (CDCl$_3$) d 4.65 (s, 1H, NHCO), 3.15 (m, 10H, 5×CH$_2$), 2.70 (t, 2H, CH$_2$NH$_2$), 1.58-1.39 (m, 39H, 6×CH$_2$, 9×CH$_3$); HRMS (FAB): theory for C$_{27}$H$_{55}$N$_4$O$_6$ (M+1), 531.4122; found (M+1), 531.4111; Anal. Calcd (C$_{27}$H$_{54}$N$_4$O$_6$.0.1H$_2$O): C, H, N.

[4-(3,4-Bis-octadec-9-enyloxy-benzylamino)-butyl]-carbamic acid tert-butyl ester (15):

To a vigorously stirred solution of the amine 9 (0.071 g, 0.38 mmol, 1.2 equiv) in CH$_2$Cl$_2$/MeOH (3:1, 5 mL) was added a solution of the aldehyde 8a (0.20 g, 0.33 mmol) in CH$_2$Cl$_2$/MeOH (3:1, 5 mL), dropwise over 20 minutes. The resulting mixture was stirred at it under an atmosphere of nitrogen overnight. $^1$H NMR showed the reaction to be complete when there was no aldehyde peak present. The solvent was removed in vacuo and the crude imine dissolved in CH$_2$Cl$_2$/MeOH (1:1, 10 mL). The solution was cooled to 0° C. and NaBH$_4$ (60 mg, 1.58 mmol) was added in 15 mg portions over 30 minutes. TLC (10% EtAc/hexane) showed the reaction to be complete after stirring overnight. The solvent was removed in vacuo and the crude oil dissolved in CH$_2$Cl$_2$ (50 mL) and washed with sodium carbonate (10% aq, 3×40 mL). The CH$_2$Cl$_2$ layer was dried over Na$_2$CO$_3$, filtered, the solvent removed in vacuo and the oily residue purified by flash column chromatography (4% MeOH/CHCl$_3$) to give the product 15 as a clear oil (0.18 g, 78%), R$_f$=0.2 (3% MeOH/CHCl$_3$). $^1$H NMR (500 MHz, CDCl$_3$) d 6.85 (s, 1H, aryl), 6.80 (m, 2H, aryl), 5.34 (t, 4H, olefinic), 4.78 (br s, 1H, NHCO), 3.97 (q, 4H, OCH$_2$), 3.69 (s, 2H, benzylic), 3.13 (m, 2H, CH$_2$) 2.63 (t, 2H, CH$_2$NH), 2.01 (m, 8H, CH$_2$C=C), 1.80 (m, 4H, CH$_2$CH$_2$O), 1.55 (m, 4H), 1.49-1.12 (m, 57H, 24×CH$_2$, 3×$\overline{C}$H$_3$), 0.89 (t, 6H, CH$_3$); $^{13}$C NMR (CDCl$_3$) d 156.17, 149.34, 148.29, 133.15, 130.11, 130.00, 120.67, 114.18, 114.08, 79.23, 69.69, 69.52, 54.12, 49.22, 40.80, 32.28, 30.16, 29.92, 29.82, 29.71, 29.67, 28.81, 28.27, 27.68, 27.60, 26.44, 23.09, 14.54; Anal. (C$_{52}$H$_{94}$N$_2$O$_4$): C, H, N.

N$^1$-(3,4-Bis-octadec-9-enyloxy-benzyl)-octane-1,8-diamine (16):

To a vigorously stirred solution of diaminooctane (0.23 g, 1.56 mmol, 5 equiv) in CH$_2$Cl$_2$/MeOH (3:1, 5 mL) was added a solution of the aldehyde 8a (0.20 g, 0.33 mmol) in CH$_2$Cl$_2$/MeOH (3:1, 5 mL), dropwise over 1 hour. The resulting mixture was stirred at RT under an atmosphere of nitrogen overnight. NMR showed the reaction to be complete when there was no aldehyde peak present in the NMR spectrum. The solvent was removed in vacuo and the crude imine dissolved in CH$_2$Cl$_2$/MeOH (1:1, 10 mL). The solution was cooled to 0° C. and sodium borohydride (60 mg, 1.58 mmol) was added in 15 mg portions over 30 minutes. TLC (10% EtAc/hexane) showed the reaction to be complete after stirring overnight. The solvent was removed in vacuo and the crude solid dissolved in CH$_2$Cl$_2$ (50 mL) and washed with sodium carbonate (10% aq, 3×40 mL). The CH$_2$Cl$_2$ layer was dried over sodium sulfate, filtered, the solvent removed in vacuo and the solid residue purified by flash column chromatography (1:10:89 NH$_4$OH:MeOH:CHCl$_3$) to give the product 16 as a white solid (0.15 g, 63%), R$_f$=0.5 (1:10:89 NH$_4$OH:MeOH:CHCl$_3$). $^1$H NMR (CDCl$_3$) d 6.85 (s, 1H, aryl), 6.80 (m, 2H, aryl), 5.34 (t, 4H, olefinic), 3.97 (q, 4H, OCH$_2$), 3.69 (s, 2H, benzylic), 2.67 (t, 2H, CH$_2$NH$_2$), 2.60 (t, 2H, CH$_2$NH$_2$), 2.01 (m, 8H, CH$_2$C=C), $\overline{1}$.80 (m, 4H, CH$_2$CH$_2$O), 1.54-1.18 (m, 56H, 28×CH$_2$), 0.88 (t, 6H, CH$_3$); $^{13}$C NMR (CDCl$_3$) d 149.31, 148.20, 133.55, 130.11, 130.00, 120.59, 114.14, 114.07, 69.70, 69.50, 54.24, 49.83, 42.60, 34.20, 32.28, 30.46, 30.16, 29.92, 29.81, 29.71, 29.67, 27.73, 27.60, 27.22, 26.44, 23.08, 14.53; HRMS (FAB): theory for C$_{51}$H$_{95}$N$_2$O$_2$ (M+1), 767.7394; found (M+1), 767.7377. Anal. (C$_{51}$H$_{94}$N$_2$O$_2$.0.3H$_2$O): C, H, N.

2-{2-[2-(3,4-Bis-octadec-9-enyloxy-benzylamino)-ethoxy]-ethoxy}-ethylamine (17):

To a vigorously stirred solution of diaminodioxaoctane (0.23 g, 1.56 mmol, 5 equiv) in CH$_2$Cl$_2$/MeOH (3:1, 5 mL) was added a solution of the aldehyde 8a (0.20 g, 0.33 mmol) in CH$_2$Cl$_2$/MeOH (3:1, 5 mL), dropwise over 1 hour. The resulting mixture was stirred at rt under an atmosphere of nitrogen overnight. NMR showed the reaction to be complete when there was no aldehyde peak present in the NMR spectrum. The solvent was removed in vacuo and the crude imine dissolved in CH$_2$Cl$_2$/MeOH (1:1, 10 mL). The solution was cooled to 0° C. and NaBH$_4$ (60 mg, 1.58 mmol) was added in 15 mg portions over 30 minutes. TLC (10% EtAc/hexane) showed the reaction to be complete after stirring overnight. The solvent was removed in vacuo and the crude oil dissolved in $CH_2Cl_2$ (50 mL) and washed with sodium carbonate (10% aq, 3×40 mL). The $CH_2Cl_2$ layer was dried over anhydrous $Na_2SO_4$, filtered, the solvent removed in vacuo and the oily residue purified by flash column chromatography (1:10:89 $NH_4OH$:MeOH:$CHCl_3$) to give the product 17 as a clear oil (0.168 g, 70%), $R_f$=0.45 (1:10:89 $NH_4OH$:MeOH:$CHCl_3$). $^1H$ NMR ($CDCl_3$) d 6.87 (s, 1H, aryl), 6.81 (m, 2H, aryl), 5.34 (t, 4H, olefinic), 3.97 (q, 4H, $OCH_2$), 3.72 (s, 2H, benzylic), 3.61 (m, 6H, $OCH_2$), 3.61 (t, 2H, $OCH_2$), 2.86 (t, 2H, $CH_2NH_2$), 2.81 (t, 2H, $CH_2NH_2$), 2.01 (m, 8H, $CH_2C$=C), 1.80 (m, 4H, $CH_2CH_2O$), 1.54-1.17 (m, 44H, 22×$CH_2$), 0.89 (t, 6H, $CH_3$); $^{13}C$ NMR ($CDCl_3$) d 149.31, 148.25, 133.11, 130.09, 129.99, 120.73, 114.26, 114.07, 73.57, 70.85, 70.57, 70.52, 69.69, 69.51, 54.02, 48.93, 42.01, 32.28, 30.15, 29.91, 29.80, 29.70, 29.67, 27.59, 26.45, 26.42, 23.07, 14.53; HRMS (FAB): theory for $C_{49}H_{91}N_2O_4$ (M+1), 771.6979; found (M+1), 771.6995; Anal. ($C_{49}H_{90}N_2O_4$): C, H, N.

(4-{[4-(3,4-Bis-octadec-9-enyloxy-benzylamino)-butyl]-tert-butoxycarbonyl-amino}-butyl)-carbamic acid tert-butyl ester (18):

To a vigorously stirred solution of the amine 12 (0.135 g, 0.38 mmol, 1.2 equiv) in $CH_2Cl_2$/MeOH (3:1, 5 mL) was added a solution of the aldehyde 8a (0.20 g, 0.33 mmol) in $CH_2Cl_2$/MeOH (3:1, 5 mL), dropwise over 20 minutes. The resulting mixture was stirred at RT under an atmosphere of nitrogen overnight. NMR showed the reaction to be complete when there was no aldehyde peak present in the NMR spectrum. The solvent was removed in vacuo and the crude imine dissolved in $CH_2Cl_2$/MeOH (1:1, 10 mL). The solution was cooled to 0° C. and sodium borohydride (60 mg, 1.58 mmol) was added in 15 mg portions over 30 minutes. TLC (10% EtAc/hexane) showed the reaction to be complete after stirring overnight. The solvent was removed in vacuo and the crude oil dissolved in $CH_2Cl_2$ (50 mL) and washed with sodium carbonate (10% aq, 3×40 mL). The $CH_2Cl_2$ layer was dried over sodium sulphate, filtered, the solvent removed in vacuo and the oily residue purified by flash column chromatography (3% MeOH/$CHCl_3$) to give the product 18 as a clear oil (0.24 g, 78%), $R_f$=0.3 (3% MeOH/$CHCl_3$). $^1H$ NMR ($CDCl_3$) d 6.85 (s, 1H, aryl), 6.80 (m, 2H, aryl), 5.34 (t, 4H, olefinic), 4.60 (br s, 1H, NHCO), 3.97 (q, 4H, $OCH_2$), 3.69 (s, 2H, benzylic), 3.13 (m, 6H, $CH_2$) 2.63 (t, 2H, $CH_2NH$), 2.01 (m, 8H, $CH_2C$=C), 1.80 (m, 4H, $CH_2CH_2O$), 1.67-1.15 (m, 70H, 26×$CH_2$, 6×$CH_3$), 0.89 (t, 6H, $CH_3$); $^{13}C$ NMR ($CDCl_3$) d 156.17, 155.71, 149.33, 148.25, 133.31, 130.11, 130.00, 120.62, 114.15, 114.08, 79.45, 69.70, 69.51, 54.13, 49.42, 47.34, 46.89, 40.58, 32.28, 30.14, 29.91, 29.80, 29.70, 29.67, 28.85, 28.79, 27.79, 27.70, 27.59, 26.42, 23.07, 14.53; HRMS (FAB): theory for $C_{61}H_{112}N_3O_6$ (M+1), 982.8551; found (M+1), 982.8510; Anal. ($C_{61}H_{111}N_3O_6$): C, H, N.

(4-{[4-(3,4-Bis-octadec-9-enyloxy-benzylamino)-butyl]-tert-butoxycarbonyl-amino}-butyl)-(4-tert-butoxycarbonylamino-butyl)-carbamic acid tert-butyl ester (19):

To a vigorously stirred solution of the amine 14 (0.20 g, 0.38 mmol, 1.2 equiv) in $CH_2Cl_2$/MeOH (3:1, 5 mL) was added a solution of the aldehyde 8a (0.20 g, 0.33 mmol) in $CH_2Cl_2$/MeOH (3:1, 5 mL), dropwise over 20 minutes. The resulting mixture was stirred at RT under an atmosphere of nitrogen overnight. NMR showed the reaction to be complete when there was no aldehyde peak present in the spectrum. The solvent was removed in vacuo and the crude imine dissolved in $CH_2Cl_2$/MeOH (1:1, 10 mL). The solution was cooled to 0° C. and sodium borohydride (60 mg, 1.58 mmol) was added in 15 mg portions over 30 minutes. TLC (10% EtAc/hexane) showed the reaction to be complete after stirring overnight. The solvent was removed in vacuo and the crude oil dissolved in $CH_2Cl_2$ (50 mL) and washed with sodium carbonate (10% aq, 3×40 mL). The $CH_2Cl_2$ layer was dried over sodium sulphate, filtered, the solvent removed in vacuo and the oily residue purified by flash column chromatography (3% MeOH/$CHCl_3$) to give the product 19 as a clear oil (0.319 g, 88%), $R_f$=0.25 (3% MeOH/$CHCl_3$). $^1H$ NMR ($CDCl_3$) d 6.85 (s, 1H, aryl), 6.80 (m, 2H, aryl), 5.34 (t, 4H, olefinic), 4.60 (br s, 1H, NHCO), 3.97 (q, 4H, $OCH_2$), 3.70 (s, 2H, benzylic), 3.14 (m, 10H, 5×$CH_2$) 2.64 (t, 2H, $CH_2NH$), 2.01 (m, 8H, $CH_2C$=C), 1.80 (m, 4H, $CH_2CH_2O$), 1.59-1.14 (m, 83H, 28×$CH_2$, 9×$CH_3$), 0.89 (t, 6H, $CH_3$); $^{13}C$ NMR ($CDCl_3$) d 156.12, 155.69, 149.33, 148.25, 133.28, 130.10, 129.99, 120.61, 114.14, 114.07, 79.40, 69.69, 69.50, 54.15, 49.47, 47.24, 46.98, 40.57, 32.27, 30.14, 29.90, 29.80, 29.69, 29.66, 28.85, 28.79, 27.77, 27.58, 26.44, 23.07, 14.53; HRMS (FAB): theory for $C_{70}H_{129}N_4O_8$ (M+1), 1153.9810; found (M+1), 1153.9840; Anal. Calcd ($C_{70}H_{128}N_4O_8$): C, H, N.

(4-{[4-(3,4-Bis-octadec-9-enyloxy-benzoylamino)-butyl]-tert-butoxycarbonyl-amino}-butyl)-carbamic acid tert-butyl ester (20):

A solution of 3,4-Bis-octadec-9-enyloxy-benzoic acid 8c (0.2 g, 0.31 mmol) in 2:1 dichloromethane/benzene (15 mL) was stirred at 0° C. for 10 min. Anhydrous DMF (2 drops) and oxalyl chloride (0.3 mL) were added in sequence and the mixture was stirred for 1 h at 0° C. The solution was concentrated in vacuo to give the crude acid chloride, 8d. Crude 8d was dissolved in $CH_2Cl_2$ (10 mL) and added dropwise to a solution of the amine 12 (0.132 g, 0.37 mmol, 1.2 equiv.) dissolved in $CH_2Cl_2$ (10 mL) and 1M NaOH (10 mL) that had been cooled to 0° C. for 15 minutes. The reaction was stirred overnight under $N_2$ at room temperature. The water layer was separated off. The $CH_2Cl_2$ layer was washed with $Na_2CO_3$ (10% aq. 3×20 mL), dried over $Na_2SO_4$, filtered, removed in vacuo and the oily residue purified by flash column chromatography (30% EtAc/hexane) to give the product 20 as a clear oil (0.261 g, 86%), $R_f$=0.25 (30% EtAc/hexane); $^1H$ NMR (500 MHz, $CDCl_3$) d 7.50-7.20 (m, 2H, phenyl), 6.90 (br s, 0.5H, NHCO), 6.81 (d, 1H, phenyl), 6.41 (br s, 0.5H, NHCO), 5.35 (t, 4H, olefinic), 4.68 (m, 1H, NHCO), 3.99 (2t, 4H, 2×$OCH_2$), 3.44 (m, 2H, $CH_2$), 3.11 (m, 6H, 3×$CH_2$), 2.00 (m, 8H, $CH_2C$=C), 1.79 (m, 4H, $CH_2CH_2O$), 1.53-1.17 (m, 70H, 26×$CH_2$, 6×$CH_3$), 0.88 (t, 6H, $CH_3$); $^{13}C$ NMR ($CDCl_3$) d 167.32, 156.18, 151.84, 148.98, 130.11, 130.09, 127.32, 113.02, 112.39, 79.62, 79.32, 69.52, 69.36, 47.09, 40.49, 39.92, 32.26, 30.13, 29.89, 29.76, 29.68, 29.65, 29.62, 29.59, 29.50, 28.84, 28.77, 27.79, 27.58, 26.38, 26.36, 23.06, 14.51; HRMS (FAB): theory for $C_{61}H_{109}N_3O_7$ (M+Na), 1018.8158; found (M+Na), 1018.8123; Anal. ($C_{61}H_{109}N_3O_7$): C, H, N.

(4-{[4-(3,4-Bis-octadec-9-enyloxy-benzoylamino)-butyl]-tert-butoxycarbonyl-amino}-butyl)-(4-tert-butoxycarbonylamino-butyl)-carbamic acid tert-butyl ester (21):

A solution of 3,4-Bis-octadec-9-enyloxy-benzoic acid 8c (0.2 g, 0.31 mmol) in 2:1 dichloromethane/benzene (15 mL) was stirred at 0° C. for 10 min. Anhydrous DMF (2 drops) and oxalyl chloride (0.3 mL) were added in sequence and the mixture was stirred for 1 h at 0° C. The solution was concentrated in vacuo to give the crude acid chloride 8d. The acid chloride 8d was dissolved in $CH_2Cl_2$ (10 mL) and added dropwise to a solution of the amine 14 (0.195 g, 0.37 mmol, 1.2 equiv.) dissolved in $CH_2Cl_2$ (10 mL) and 1M NaOH (10 mL) that had been cooled to 0° C. for 15 minutes. The reaction was stirred overnight under $N_2$ at room temperature. The water layer was separated off. The $CH_2Cl_2$ layer was washed with $Na_2CO_3$ (10% aq. 3×20 mL), dried over $Na_2SO_4$, filtered, removed in vacuo and the oily residue purified by flash column chromatography (30% EtAc/hexane) to give the product 21 as a clear oil (0.295 g, 83%), $R_f$=0.20 (30% EtAc/hexane); $^1$H NMR (500 MHz, CDCl$_3$) d 7.42-7.20 (m, 2H, phenyl), 6.82 (br s, 0.5H, NHCO), 6.80 (d, 1H, phenyl), 6.39 (br s, 0.5H, NHCO), 5.35 (t, 4H, olefinic), 4.65 (m, 1H, NHCO), 3.99 (2×t, 4H, 2×OCH$_2$), 3.42 (m, 2H, CH$_2$), 3.13 (m, 10H, 5×CH$_2$), 2.00 (m, 8H, CH$_2$C=C), 1.79 (m, 4H, CH$_2$CH$_2$O), 1.53-1.17 (m, 83H, 28×CH$_2$, 9×CH$_3$), 0.88 (t, 6H, CH$_3$); $^{13}$C NMR (CDCl$_3$) d 167.35, 156.16, 155.73, 151.88, 148.99, 130.13, 130.11, 127.37, 113.05, 112.41, 79.54, 69.54, 69.38, 47.03, 40.58, 39.97, 32.27, 30.14, 29.90, 29.77, 29.69, 29.66, 29.63, 29.60, 29.51, 28.85, 28.79, 27.78, 27.59, 26.40, 26.37, 23.07, 14.53; HRMS (FAB): theory for C$_{70}$H$_{126}$N$_4$O$_9$ (M+Na), 1189.9407; found (M+Na), 1189.9365; Anal. (C$_{70}$H$_{126}$N$_4$O$_8$): C, H, N.

N$^1$-(3,4-Bis-octadec-9-enyloxy-benzyl)-butane-1,4-diamine, dihydrochloride salt (22):

A concentrated solution of the amine 15 (0.158 g, 0.19 mmol) in ethyl acetate was added cooled to 0° C. A total of 4 mL of a freshly prepared saturated solution of HCl in ethyl acetate was added dropwise and the solution stirred for 1 h at room temperature during which time a white precipitate formed. The ethyl acetate was removed in vacuo and the residue co-evaporated with ethyl acetate and chloroform to give the product 22 as an off white powder (0.15 g, 98%); $^1$H NMR (500 MHz, CDCl$_3$) d 9.50 (br s, 2H, R$_2$N$^+$H$_2$), 8.22 (br s, 3H, RN$^+$H$_3$), 7.24 (s, 1H, aryl), 7.05 (d, 1H, aryl), 6.82 (d, 1H, aryl), 5.34 (m, 4H, olefinic), 4.02 (q, 4H, OCH$_2$), 3.93 (t, 2H, benzylic), 3.07 (m, 2H, CH$_2$) 2.81 (m, 2H, CH$_2$), 2.01 (m, 8H, CH$_2$C=C), 1.95 (m, 2H, CH$_2$), 1.85 (m, 2H, CH$_2$), 1.78 (m, 4H, CH$_2$CH$_2$O), 1.45 (m, 4H, 2×CH$_2$), 1.38-1.20 (m, 40H, 20×CH$_2$), 0.89 (t, 6H, CH$_3$); $^{13}$C NMR (300 MHz, CDCl$_3$) d 150.00, 149.37, 130.12, 130.09, 129.95, 122.58, 115.81, 113.49, 69.63, 69.38, 51.44, 51.06, 45.80, 39.63, 32.29, 30.24, 30.21, 30.16, 30.00, 29.93, 29.71, 27.61, 26.63, 26.49, 24.83, 23.75, 23.08, 14.54; HRMS (FAB): theory for C$_{47}$H$_{87}$N$_2$O$_2$ (M+1), 711.6768; found (M+1), 711.6827; Anal. (C$_{47}$H$_{88}$Cl$_2$N$_2$O$_4$.1.2H$_2$O): C, H, N.

N$^1$-(3,4-Bis-octadec-9-enyloxy-benzyl)-octane-1,8-diamine, dihydrochloride salt (23):

A concentrated solution of the amine 16 (0.097 g, 0.13 mmol) in ethyl acetate was added cooled to 0° C. A total of 4 mL of a freshly prepared saturated solution of HCl in ethyl acetate was added dropwise and the solution stirred for 1 h at room temperature during which time a white precipitate formed. The ethyl acetate was removed in vacuo and the residue co-evaporated with ethyl acetate and chloroform to give the product 23 as an off white powder (0.104 g, 98%); $^1$H NMR (CDCl$_3$) d 7.24 (s, 1H, aryl), 7.05 (d, 1H, aryl), 6.85 (d, 1H, aryl), 5.35 (m, 4H, olefinic), 4.07 (q, 4H, OCH$_2$), 3.95 (t, 2H, benzylic), 3.07 (m, 2H, CH$_2$) 2.79 (m, 2H, CH$_2$), 2.05 (m, 8H, CH$_2$C=C), 1.82 (m, 8H, CH$_2$CH$_2$O, 2×CH$_2$), 1.58-1.21 (m, 52H, 26×CH$_2$), 0.89 (t, 6H, CH$_3$); $^{13}$C NMR (300 MHz, CDCl$_3$) d 149.36, 148.78, 130.85, 130.33, 129.74, 122.23, 115.56, 113.45, 69.56, 69.32, 51.56, 51.15, 45.96, 39.86, 32.53, 30.44, 30.44, 30.23, 30.12, 30.00, 29.71, 27.61, 27.51, 27.10, 26.83, 26.69, 24.82, 23.77, 23.08, 14.54; HRMS (FAB): theory for C$_{51}$H$_{95}$N$_2$O$_2$ (M+1), 767.7394; found (M+1), 767.7419; Anal. (C$_{51}$H$_{96}$Cl$_2$N$_2$O$_2$.0.3H$_2$O): C, H, N.

2-{2-[2-(3,4-Bis-octadec-9-enyloxy-benzylamino)-ethoxy]-ethoxy}-ethylamine, dihydrochloride salt (24):

A concentrated solution of the amine 17 (0.14 g, 0.18 mmol) in ethyl acetate was added cooled to 0° C. A total of 4 mL of a freshly prepared saturated solution of HCl in ethyl acetate was added dropwise and the solution stirred for 1 h at room temperature. The ethyl acetate was removed in vacuo and the residue co-evaporated with ethyl acetate and chloroform to give the product 24 as an off white powder (0.15 g, 98%); $^1$H NMR (CDCl$_3$) d 7.27 (s, 1H, aryl), 7.00 (d, 1H, aryl), 6.82 (d, 1H, aryl), 5.33 (m, 4H, olefinic), 4.14 (m, 2H, benzylic), 4.01 (t, 2H, OCH$_2$), 3.95 (t, 2H, OCH$_2$), 3.87 (t, 2H, CH$_2$), 3.78 (t, 2H, CH$_2$), 3.70 (t, 4H, CH$_2$), 3.25 (t, 2H, CH$_2$) 2.93 (m, 2H, CH$_2$), 2.02 (m, 8H, CH$_2$C=C), 1.89 (m, 4H, CH$_2$CH$_2$O), 1.53-1.18 (m, 44H, 22×CH$_2$), 0.89 (t, 6H, CH$_3$); $^{13}$C NMR (300 MHz, CDCl$_3$) d 149.91, 149.62, 130.12, 130.00, 123.28, 122.61, 115.46, 113.63, 70.22, 70.09, 69.64, 69.40, 66.50, 65.98, 51.06, 45.08, 40.11, 32.28, 30.15, 29.92, 29.70, 27.60, 26.54, 26.43, 23.07, 14.54; HRMS (FAB): theory for C$_{49}$H$_{91}$N$_2$O$_4$ (M+1), 771.6973; found (M+1), 771.6967; Anal. (C$_{49}$H$_{92}$Cl$_2$N$_2$O$_4$.0.4H$_2$O): C, H, N.

N-(4-Amino-butyl)-N'-(3,4-bis-octadec-9-enyloxy-benzyl)-butane-1,4-diamine, tri hydrochloride salt (25):

A concentrated solution of the amine 18 (0.17 g, 0.17 mmol) in ethyl acetate was added cooled to 0° C. A total of 4 mL of a freshly prepared saturated solution of HCl in ethyl acetate was added dropwise and the solution stirred for 1 h at room temperature during which time a white precipitate formed. The ethyl acetate was removed in vacuo and the residue co-evaporated with ethyl acetate and chloroform to give the product 25 as a white powder (0.151 g, 98%); $^1$H NMR (CDCl$_3$/CH$_3$OD 9:1) d 7.13 (s, 1H, aryl), 7.02 (d, 1H, aryl), 6.85 (d, 1H, aryl), 5.33 (m, 4H, olefinic), 4.05 (m, 2H, benzylic), 3.97 (t, 2H, OCH$_2$), 3.04 (m, 6H, 3×CH$_2$) 2.93 (m, 2H, CH$_2$), 2.02 (m, 8H, CH$_2$C=C), 1.90 (m, 8H, 4×CH$_2$), 1.81 (m, 4H, CH$_2$CH$_2$O), 1.47 (m, 4H, 2×CH$_2$), 1.40-1.17 (m, 40H, 20×CH$_2$), 0.89 (t, 6H, CH$_3$); $^{13}$C NMR (300 MHz, D$_2$O) δ 148.94, 148.33, 129.26, 129.19, 123.64, 122.52, 113.10, 68.50, 68.39, 49.96, 45.98, 45.43, 39.86, 31.28, 29.18, 29.11, 28.93, 28.86, 28.70, 28.62, 26.64, 26.59, 25.68, 25.62, 24.00, 22.54, 22.46, 22.11, 13.89; HRMS (FAB): theory for C$_{51}$H$_{96}$N$_3$O$_2$ (M+1), 782.7497; found (M+1), 782.7495; Anal. (C$_{51}$H$_{95}$Cl$_3$N$_3$O$_2$.0.6H$_2$O): C, H, N.

N-[4-(4-Amino-butylamino)-butyl]-N'-(3,4-bis-octadec-9-enyloxy-benzyl)-butane-1,4-diamine, tetrahydrochloride salt (26):

A concentrated solution of the amine 19 (0.253 g, 0.22 mmol) in ethyl acetate was added cooled to 0° C. A total of 5 mL of a freshly prepared saturated solution of HCl in ethyl acetate was added dropwise and the solution stirred for 1 h at room temperature during which time a white precipitate formed. The ethyl acetate was removed in vacuo and the residue co-evaporated with ethyl acetate and chloroform to give the product 26 as a white powder (0.215 g, 98%); $^1$H NMR (CD$_3$OD) δ 7.13 (s, 1H, aryl), 7.04 (d, 1H, aryl), 6.98 (d, 1H, aryl), 5.33 (t, 4H, olefinic), 4.12 (m, 2H, benzylic), 4.03 (t, 2H, OCH$_2$), 3.99 (t, 2H, OCH$_2$), 3.08 (m, 10H, 5×CH$_2$), 2.98 (t, 2H, CH$_2$), 2.02 (m, 8H, CH$_2$C=C), 1.89 (m, 16H, 8×CH$_2$), 1.47 (m, 4H, 2×CH$_2$), 1.42-1.19 (m, 40H, 20×CH$_2$), 0.89 (t, 6H, CH$_3$); $^{13}$C NMR (300 MHz, D$_2$O) δ 149.74, 148.90, 129.62, 129.46, 123.92, 123.71, 69.36, 68.88, 51.12, 46.68, 38.99, 32.14, 29.97, 29.81, 29.60, 27.36, 26.53, 24.69, 24.22, 23.14, 23.06, 22.84, 14.05; HRMS (FAB): theory for C$_{55}$H$_{105}$N$_4$O$_2$ (M+1), 853.8238; found (M+1), 853.8264; Anal. (C$_{55}$H$_{109}$Cl$_4$N$_4$O$_2$.0.6H$_2$O): C, H, N.

N-[4-(4-Amino-butylamino)-butyl]-3,4-bis-octadec-9-enyloxy-benzamide, dihydrochloride salt (27):

A concentrated solution the amide 20 (0.22 g, 0.22 mmol) in ethyl acetate was added cooled to 0° C. A total of 5 mL of a freshly prepared saturated solution of HCl in ethyl acetate was added dropwise and the solution stirred for 1 h at room temperature during which time a white precipitate formed. The ethyl acetate was removed in vacuo and the residue co-evaporated with ethyl acetate and chloroform to give the product 27 as a white powder (0.19 g, 98%); $^1$H NMR (CDCl$_3$) d 8.95 (br s, 2H, R$_2$N$^+$H$_2$), 8.20 (br s, 3H, RN$^+$H$_3$), 7.45 (m, 2H, aryl), 6.78 (m, 1H, aryl), 5.33 (m, 4H, olefinic), 3.95 (m, 4H, OCH$_2$), 3.38 (m, 2H, CH$_2$), 3.11 (m, 2H, CH$_2$), 3.01 (m, 4H, 2×CH$_2$), 2.08-1.89 (m, 14H, 7×CH$_2$), 1.71 (m, 6H, 3×CH$_2$), 1.47-1.18 (m, 44H, 20×CH$_2$), 0.89 (t, 6H, CH$_3$); HRMS (FAB): theory for C$_{51}$H$_{94}$N$_3$O$_3$ (M+1), 796.7290; found (M+1), 796.7249; Anal. (C$_{51}$H$_{95}$Cl$_2$N$_3$O$_3$.1.6H$_2$O): C, H, N.

N-{4-[4-(4-Amino-butylamino)-butylamino]-butyl}-3,4-bis-octadec-9-enyloxy-benzamide, trihydrochloride salt (28):

A concentrated solution of the amide 21 (0.22 g, 0.19 mmol) in ethyl acetate was added cooled to 0° C. A total of 5 mL of a freshly prepared saturated solution of HCl in ethyl acetate was added dropwise and the solution stirred for 1 h at room temperature during which time a white precipitate formed. The ethyl acetate was removed in vacuo and the residue co-evaporated with ethyl acetate and chloroform to give the product 28 as a white powder (0.18 g, 98%); $^1$H NMR (CDCl$_3$/CH$_3$OD 9:1) d 7.42 (m, 2H, aryl), 6.78 (m, 1H, aryl), 5.33 (m, 4H, olefinic), 4.03 (m, 4H, OCH$_2$), 3.41 (m, 2H, CH$_2$), 3.01 (m, 10H, 5×CH$_2$), 2.08-1.66 (m, 24H, 12×CH$_2$), 1.71 (m, 6H, 3×CH$_2$), 1.56-1.13 (m, 44H, 20×CH$_2$), 0.89 (t, 6H, CH$_3$); HRMS (FAB): theory for C$_{55}$H$_{105}$N$_4$O$_3$ (M+1), 867.8025; found (M+1), 867.8022; Anal. Calcd for (C$_{55}$H$_{105}$Cl$_3$N$_4$O$_3$.1.5H$_2$O): C, H, N.

Advantages of the present invention include the surprising discovery that compound (#26) is much more efficient in delivering DNA into a target cell than the commercial Lipofectamine™ transfection agent.[39] This efficiency, coupled with the straightforward synthesis we developed for this material makes this product commercially viable to pursue.

Uses of compound #26 and other compounds herein disclosed include use as smart anticancer agents which recognize and selectively deliver "cargoes" to specific cell types. The cargoes could be either 'corrective' DNA which repairs or replaces the cancerous genetic lesion and allows for the cell to heal itself. Alternatively, one could deliver toxic compounds such as the plant toxin saporin, which targets cell protein synthesis ability. Blocking protein synthesis is a toxic event for the cell. Therefore, one could envision delivering toxic compounds selectively to cancer cells to kill them, even in the presence of normal healthy cells. Coadministration of the agent saporin with a lipopolyamine was shown to promote entry of the agent into cells by the cell's own polyamine transporter system. These results were published in FEBS J., 274 (2007) 4825-4836, a paper which is noted above and which has been incorporated herein by reference in its entirety.

A deficiency in previously known compounds is their lower efficiency of transfection and their inability to target specific cell types via the polyamine transport system.

EXAMPLES

I.

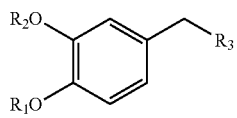

1

$R_1$ and $R_2$ may be the same or may be different and comprise a long hydrocarbon chain which is between six and eighteen carbons long and either contains or does not contain units of unsaturation. For example, the chain could be derived from the C$_{18}$ oleic acid and attached via an ester linkage or via an ether linkage and an oleyl group. The chains can range from lauryl, stearic, myristic and oleic acids.

$R_3$ is a polycation comprising a polyamine side chain. These aliphatic polyamine side chains can range from mono amines to octaamines with carbon spacer groups ranging from two to six in between the nitrogen centers. These can also be branched systems as well. For example:

$R_3$=—NH$_2$

—NHCH$_3$

—NHCH$_2$CH$_3$

—NH—(CH$_2$)$_a$NH$_2$

—NH—(CH$_2$)$_a$NH(CH$_2$)$_b$NH$_2$

—NH—(CH$_2$)$_a$NH(CH$_2$)$_b$NH(CH$_2$)$_c$NH$_2$

—NH—(CH$_2$)$_a$NH(CH$_2$)$_b$NH(CH$_2$)$_c$NH(CH$_2$)$_d$NH$_2$

—NH—(CH$_2$)$_a$NH(CH$_2$)$_b$NH(CH$_2$)$_c$NH(CH$_2$)$_d$NH(CH$_2$)$_e$NH$_2$

—NH—(CH$_2$)$_a$NH(CH$_2$)$_b$NH(CH$_2$)$_c$NH(CH$_2$)$_d$NH(CH$_2$)$_e$NH(CH$_2$)$_f$NH$_2$

—NH—(CH$_2$)$_a$NH(CH$_2$)$_b$NH(CH$_2$)$_c$NH(CH$_2$)$_d$NH(CH$_2$)$_e$NH(CH$_2$)$_f$NH(CH$_2$)$_g$NH$_2$ where a-g range from two to six Note: other polycationic moieties may be used in place of the polyamine. More biofriendly cations like polyhistine, polyarginine, polylysine or polyornithine peptides could be used. These could be in the all L, all D or mixed L,D forms. In addition, the hydrochloride salts as well as other pharmaceutically acceptable salt forms of compound 1 could be used.

II.

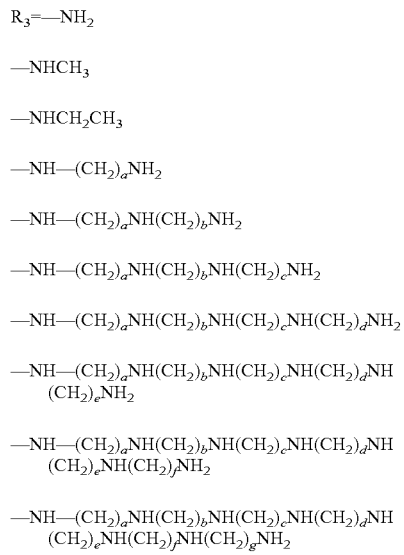

2

$R_1$ and $R_2$ are the same or different and are comprised of a long hydrocarbon chain which is between six and eighteen carbons long and either contains or does not contain units of unsaturation. For example, the chain could be derived from the C$_{18}$ oleic acid and attached via an ester linkage or via an ether linkage and an oleyl group. The chains can range from lauryl, stearic, myristic and oleic acids.

$R_3$ is a polycations comprised of a polyamine side chain. These aliphatic polyamine side chains can range from mono amines to octaamines with carbon spacer groups ranging from two to six in between the nitrogen centers. These can also be branched systems as well.

$R_3$=—NH$_2$

—NHCH$_3$

—NHCH$_2$CH$_3$

—NH—(CH$_2$)$_a$NH$_2$

—NH—(CH$_2$)$_a$NH(CH$_2$)$_b$NH$_2$

—NH—(CH$_2$)$_a$NH(CH$_2$)$_b$NH(CH$_2$)$_c$NH$_2$

—NH—(CH$_2$)$_a$NH(CH$_2$)$_b$NH(CH$_2$)$_c$NH(CH$_2$)$_d$NH$_2$

—NH—(CH$_2$)$_a$NH(CH$_2$)$_b$NH(CH$_2$)$_c$NH(CH$_2$)$_d$NH(CH$_2$)$_e$NH$_2$

—NH—(CH$_2$)$_a$NH(CH$_2$)$_b$NH(CH$_2$)$_c$NH(CH$_2$)$_d$NH(CH$_2$)$_e$NH(CH$_2$)$_f$NH$_2$

—NH—(CH$_2$)$_a$NH(CH$_2$)$_b$NH(CH$_2$)$_c$NH(CH$_2$)$_d$NH(CH$_2$)$_e$NH(CH$_2$)$_f$NH(CH$_2$)$_g$NH$_2$ where a-g range from two to six Note: other polycationic moieties may be used in place of the polyamine. More biofriendly cations like poly-histine, polyarginine, polylysine or polyornithine peptides could be used. These could be in the all L, all D or mixed L,D forms. In addition, the hydrochloride salts as well as other pharmaceutically acceptable salt forms of 2 could be used as well.

III. Pharmaceutical compositions of either 1 and/or 2 along with a neutral lipid (e.g., DOPE) and a therapeutic agent such as a DNA plasmid, siRNA (gene silencing agent), or toxic compound. The DNA plasmid could be a corrective gene to repair or replace a damaged gene within the cell. The siRNA could be a RNA molecule designed to silence a bad gene to provide a positive therapeutic outcome. The toxic compound could be a toxic drug that kills the cell like methotrexate, doxorubicin, cis platin, taxol, or other toxins like saporin or ricin which target specific critical cell functions.

Summary. The invention will allow for the selective delivery of therapeutic agents to cancer cells via the polyamine transport system. The technology is predicated upon the fact that certain cancer cells readily import polyamines from their environment. This property provides an opportunity to target these cells via their selective uptake of these cationic materials. The patented materials can also delivery other therapeutic agents to cells such as DNA plasmids, RNA for gene silencing therapies, and proteins which repair or destroy cells. The technology also allows for enhanced transfection of cells by utilizing this special uptake pathway to deliver new genes, nucleic acids and proteins into cells.

Accordingly, in the drawings and specification there have been disclosed typical preferred embodiments of the invention and although specific terms may have been employed, the terms are used in a descriptive sense only and not for purposes of limitation. The invention has been described in considerable detail with specific reference to these illustrated embodiments. It will be apparent, however, that various modifications and changes can be made within the spirit and scope of the invention as described in the foregoing specification and as defined in the appended claims.

REFERENCES

1. Lander, E. S.; Linton, L. M.; Birren, B.; Nusbaum, C.; Zody, M. C.; Baldwin, J.; Devon, K.; Dewar, K.; Doyle, M.; FitzHugh, W.; Funke, R. et al. Initial sequencing and analysis of the human genome. *Nature,* 2001, 409, 860-921.
2. Venter, J. C., Adams, M. D., Myers, E. W. et al. The Sequence of the Human Genome *Science,* 2001, 291, 1304-1351.
3. Feigner, P. L.; Rhodes, G. Gene Therapeutics. *Nature* 1991, 349, 351-352.
4. Smythe-Templeton, N.; Lasic, D. D., Eds. *Gene Therapy. Therapeutic Mechanisms and Strategies*; Marcel Dekker Inc.: New York, 2000.
5. a) Cogoni, C.; Macino, G. Post-transcriptional gene silencing across kingdoms. *Genes Dev* 2000, 10, 638-643; b) Guru T. A silence that speaks volumes. *Nature* 2000. 404, 804-808; c) Hammond, S. M,; Caudy, A. A.; Hannon, G. J. Post-transcriptional Gene Silencing by Double-stranded RNA. *Nature Rev Gen.* 2001, 2, 110-119; d) Gitlin. L.; Karelsky, S.; Andino, R. Short interfering RNA confers intracellular antiviral immunity in human cells *Nature* 2002, 418, 430-434.
6. Wang, D.; Zheng, F.; Holmberg, S.; Kohlhaw, G. B. Yeast Transcriptional Regulator Leu3p ?self-masking, specificity of masking, and evidence for regulation by the intracellular level of Leu3p. *J. Biol. Chem.,* 1999, 274, 19017-19024.
7. Chisaka, O.; Capecchi, M. R. Regionally restricted developmental defects resulting from targeted disruption of the mouse homeobox gene hox-1.5. *Nature* 1991, 350, 473-479.
8. Smith, A. E. Viral Vectors in Gene Therapy. *Annu. Rev. Microbiol.* 1995, 49, 807-838.
9. Kay, M. A.; Glorioso, J. C.; Naldini, L. Viral vectors for gene therapy: the art of turning infectious agents into vehicles of therapeutics. *Nat. Med.* 2001, 7, 33-40.
10. Feigner, P. L.; Gadek, T. R.; Holm, M.; Roman, R.; Chan, H. W.; Wenz, M.; Northrop, J. P.; Ringold; G. M.; Danielsen, M. Lipofectin: A highly efficient, lipid-mediated DNA-transfection procedure. *Proc. Natl. Acad. Sci. USA.* 1987, 84, 7413-7417.
11. Behr, J. P.; Demeneix, B.; Loeffler, J-P.; Perez-Mutul, J. Efficient gene transfer into mammalian primary endocrine cells with lipopolyamine-coated DNA. *Proc. Natl. Acad. Sci. USA.* 1989, 86, 6982-6986.
12. Boussif, O.; Lezoualc'h, F.; Zanta, M. A.; Mergny, M. D.; Scherman, D.; Demeneix, B.; Behr, J. P. A versatile vector for gene and oligonucleotide transfer into cells in culture and in vivo: Polyethylenimine. *Proc. Natl. Acad. Sci. USA.* 1995, 92, 7297-7301.
13. Wheeler, C. J.; Feigner, P. L.; Tsai, Y. J.; Marshall, J.; Sukhu, L.; Doh, S. G.; Hartikka, J.; Nietupski, J.; Manthorpe, M.; Nichols, M.; Plewe, M.; Liang, X.; Norman, J., Smith, A.; Cheng, S. A novel cationic lipid greatly enhances plasmid DNA delivery and expression in mouse lung. *Proc. Natl. Acad. Sci. USA.* 1996, 93, 11454-11459.
14. Remy, J-S.; Sirlin, C.; Vierling, P.; Behr, J. P. Gene Transfer with a Series of Lipophilic DNA-Binding molecules. *Bioconjugate Chem.* 1994, 5, 647-654.
15. Miller. A. D. Cationic Liposomes for Gene Therapy. *Angew. Chem. Int. Ed.* 1998, 37, 1768-1785.
16. Ilies, M. A.; Balaban, A. T. Recent developments in cationic lipid-mediated gene delivery and gene therapy. *Expert Opin. Ther. Patents.* 2001, 11, 1729-1752.
17. Ilies, M. A.; Seitz, W. A.; Balaban, A. T. Cationic Lipids in Gene Delivery: Principles, Vector Design and Therapeutical Applications. *Curr. Pharm. Design.* 2002, 8, 2441-2473.
18. a) Hemant, D. M.; Huang, L. Liposome and polylysine mediated gene transfer. *New J. Chem.* 1997, 21, 113-124; b) Halley-Nelson, P.; Ciccarone, V.; Geheyehu, G.; Jessee, J.; Feigner, P. L. LipofectAMINE reagent: a new higher efficiency polycationic liposome transfection reagent. *Focus* 1993, 15, 73-83. 19. Vigneron, J. P.; Oudrhiri, N.;

Fauquet, M.; Vergely, L.; Bradley, J. C.; Basseville, M.; Lehn, P.; Lehn, J. M. *Proc. Natl. Acad. Sci. USA.* 1996, 93, 9682.

20. Rothbard, J. B.; Kreider, E.; VanDeusen, C. L.; Wright, I.; Wylie, B. L.; Wender, P. A. Arginine-Rich Molecular Transporters for Drug Delivery: Role of Backbone Spacing in Cellular Uptake. *J. Med. Chem.*, 2002, 45, 3612-3618.

21. Byk, G.; Dubertret, C.; Escriou, V.; Frederic, M.; Jaslin, G.; Rangara, R.; Pitard, B.; Crouzet, J.; Wils, P.; Schwartz, B.; Scherman, D. Synthesis, Activity, and Structure-Activity Relationship Studies of Novel Cationic Lipids for DNA Transfer. *J. Med. Chem.* 1998, 41, 224-235.

22. Behr, J. P. DNA strongly binds to micelles and vesicles containing lipopolyamines or lipointercalants. *Tetrahedron Lett.* 1986, 27, 5861-5864.

23. Schulze, U.; Schmidt, H. W.; Safinya, C. R. Synthesis of Novel Cationic Poly(Ethylene Glycol) Containing Lipids. *Bioconjugate Chem.* 1999, 10, 548-552

24. Ewert, K.; Ahmad, A.; Evans, H. M.; Schmidt, H.-W.; Safinya, C. R. Efficient Synthesis and Cell-Transfection Properties of a New Multivalent Cationic Lipid for Nonviral Gene Delivery. *J. Med. Chem.* 2002, 45, 5023-5029.

25. Wang, C.; Delcros, J.-G.; Cannon, L.; Konate, F.; Carias, H.; Biggerstaff, J.; Gardner, R. A.; Phanstiel, O., IV. Defining the Molecular Requirements for the Selective Delivery of Polyamine Conjugates into Cells Containing Active Polyamine Transporters. *J. Med. Chem.* 2003, 46, 5129-5138.

26. Wang, C.; Delcros, J.-G.; Biggerstaff, J.; Phanstiel, O., IV; Synthesis and Biological Evaluation of $N^1$-(Anthracen-9-ylmethyl)triamines as Molecular Recognition Elements for the Polyamine Transporter. *J. Med. Chem.* 2003, 46, 2663-2671.

27. Wang, C.; Delcros, J.-G.; Biggerstaff, J.; Phanstiel, O., IV. Molecular Requirements for Targeting the Polyamine Transport System. Synthesis and Biological Evaluation of Polyamine-Anthracene Conjugates. *J. Med. Chem.* 2003, 46, 2672-2682.

28. Gardner, R. A.; Delcros, J-G.; Konate, F.*; Breitbeil III, F.; Martin, B.; Sigman, M.; Huang, M.; Phanstiel IV, O. $N^1$-Substituent Effects in the Selective Delivery of Polyamine-Conjugates into Cells Containing Active Polyamine Transporters, *J. Med. Chem.* 2004, 47, 6055-6069.

29. Breitbeil III, F. Kaur, N.; Delcros, J-G.; Martin, B.; Abboud, K. A.; Phanstiel IV, O. Modeling the Preferred Shapes of Polyamine Transporter Ligands and Dihydromotuporamine-C Mimics: Shovel versus Hoe, *J. Med. Chem.* 2006, 49, 2407-2416.

30. Wang, C.; Abboud, K. A.; Phanstiel, O., I. Synthesis and Characterization of N1-(4-Toluenesulfonyl)-N1-(9-anthracenemethyl)triamines. *J. Org. Chem.* 2002, 67, 7865-7868.

31. Phanstiel, O., IV; Price, H. L.; Wang, L.; Juusola, J.; Kline, M.; Shah, S. M. The Effect of Polyamine Homologation on the Transport and Cytotoxicity Properties of Polyamine-(DNA-Intercalator) Conjugates. *J. Org. Chem.* 2000, 65, 5590-5599.

32. Wang, L.; Price, H. L.; Juusola, J.; Kline, M.; Phanstiel, O., IV. Influence of Polyamine Architecture on the Transport and Topoisomerase II Inhibitory Properties of Polyamine DNA-Intercalator Conjugates. *J. Med. Chem.* 2001, 44, 3682-3691.

33. a) Lipofectamine 2000 is a proprietary formulation of Invitrogen, Inc. Lipofectamine itself is a 3:1 ratio (w/w) of compounds 4 and 6; b) Floch, V.; Bolc'h, G. L.; Audrézet, M-P., Yaouanc, J.-J.; Clément, J.-C.; des Abbayes, H.; Mercier, B.; Abgrall, J.-F.; Férec, C. Cationic Phosphonolipids as non Viral Vectors for DNA transfection in Hematopoietic Cell lines and CD34$^+$ cells. *Blood Cells, Molecules and Diseases* 1997, 23, No. 5, 69-87.

34. Gardner, R. A.; Kinkade, R.; Wang, C.; Phanstiel IV, O. Total Synthesis of Petrobactin and Its Homologues as Potential Growth Stimuli for *Marinobacter hydrocarbonoclasticus*, an oil-degrading bacteria. *J. Org. Chem.* 2004, 69, 3530-3537.

35. Desmukh, H. M; Huang, L. Liposome and polylysine mediated gene transfer. *New J. Chem.* 1997, 21, 113-124 and references therein.

36. Ahmed, O. A. A.; Adjimatera, N.; Pourzand, C.; Blagbrough, I. S, N4,N9-Dioleoylspermine is a novel nonviral lipopolyamine vector for Plasmid DNA Formulation. *Pharm. Res.* 2005, 22, 972-980.

37. Belting, M.; Persson, S.; Fransson, L.-Å. Proteoglycan involvement in polyamine uptake. *Biochem. J.* 1999, 338, 317-323.

38. Mosmann, T. Rapid colorimetric assay for cellular growth and survival: application to proliferation and cytotoxicity assays. *J. Immunol. Methods* 1983, 65, 55-63.

39. Gardner, R. A., Belting. M., Svensson, K Phanstiel, O. Synthesis and Transfection Efficiencies of New Lipophilic Polyamines, J. Med. Chem. Jan. 25, 2007, 50: 308-318.

That which is claimed:

1. A vector effective in delivering an agent into a cell, said vector comprising a cationic lipid selected from compounds (25), (26), (27), (28), their pharmaceutically acceptable salts and combinations thereof.

2. The vector of claim 1, wherein said agent comprises a polynucleotide.

3. The vector of claim 1, wherein said agent comprises DNA.

4. The vector of claim 1, wherein Said agent comprises a transgene.

5. The vector of claim 1, wherein said agent is toxic for the cell.

6. A polyamine cationic lipid selected from compounds 25), (26), (27), (28), their pharmaceutically acceptable salts and combinations thereof.

7. The lipid of claim 6, wherein the selected compound is compound (26) or a pharmaceutically acceptable salt thereof.

8. A polyamine cationic lipid vector effective in delivering an agent into a cell in enhanced levels by being recognized by the cell's polyamine transport system, said vector comprising compound (26) or a pharmaceutically acceptable salt thereof.

9. The vector of claim 8, wherein said agent comprises a polynucleotide.

10. The vector of claim 8, wherein said agent comprises DNA.

11. The vector of claim 8, wherein said agent comprises a transgene.

12. The vector of claim 8, wherein said agent is toxic for the cell.

13. A method of delivering an agent into a cell, the method comprising associating the agent with a polyamine cationic lipid selected from compounds (25), (26), (27), (28), their pharmaceutically acceptable salts and combinations thereof and contacting the cell therewith.

14. The method of claim 13, wherein said agent comprises a polynucleotide.

15. The method of claim 13, wherein said agent comprises DNA.

16. The method of claim 13, wherein said agent comprises a transgene.

17. The method of claim 16, wherein said agent is toxic for the cell.

18. A method of delivering enhanced levels of an agent into a cell, the method comprising associating the agent with a polyamine cationic lipid according to compound (26) or a pharmaceutically acceptable salt thereof and effective in being recognized by a polyamine transport system in the cell.

19. The method of claim 18, wherein said agent comprises a polynucleotide.

20. The method of claim 18, wherein said agent comprises DNA.

21. The method of claim 18, wherein said agent comprises a transgene.

22. The method of claim 18, wherein said agent is toxic for the cell.

23. A method of delivering enhanced levels of an agent into target cells having an upregulated polyamine transporter, the target cells being among a population of normal cells, the method comprising associating the agent with a polyamine cationic lipid according to compound (26) or a pharmaceutically acceptable salt thereof and contacting the cell population therewith so as to preferentially deliver the polynucleotide into the target cells via the upregulated polyamine transporter system.

24. The method of claim 23, wherein said agent comprises a polynucleotide.

25. The method of claim 23, wherein said agent comprises DNA.

26. The method of claim 23, wherein said agent comprises a transgene.

27. The method of claim 23, wherein said agent is toxic for the cell.

28. A method of treating a target cell having an upregulated polyamine transporter, the method comprising associating an agent with a polyamine cationic lipid according to compound (26) or a pharmaceutically acceptable salt thereof and contacting the cell therewith.

29. The method of claim 28, wherein said agent comprises a polynucleotide.

30. The method of claim 28, wherein said agent comprises DNA.

31. The method of claim 28, wherein said agent comprises a transgene.

32. The method of claim 28, wherein said agent is toxic for the cell.

\* \* \* \* \*